(12) United States Patent
Syed et al.

(10) Patent No.: US 10,682,562 B2
(45) Date of Patent: Jun. 16, 2020

(54) AUTONOMOUS PERSONALIZED GOLF RECOMMENDATION AND ANALYSIS ENVIRONMENT

(71) Applicant: Arccos Golf, LLC, Stamford, CT (US)

(72) Inventors: Salman Hussain Syed, Stamford, CT (US); Colin David Phillips, Stratford, CT (US)

(73) Assignee: Arccos Golf LLC, Stamford, CT (US)

( * ) Notice: Subject to any disclaimer, the term of this patent is extended or adjusted under 35 U.S.C. 154(b) by 180 days.

(21) Appl. No.: 15/872,601

(22) Filed: Jan. 16, 2018

(65) Prior Publication Data

US 2018/0200605 A1    Jul. 19, 2018

Related U.S. Application Data

(60) Provisional application No. 62/447,221, filed on Jan. 17, 2017.

(51) Int. Cl.
| | |
|---|---|
| *A63B 71/06* | (2006.01) |
| *A63B 60/46* | (2015.01) |
| *A63B 24/00* | (2006.01) |
| *G06N 3/08* | (2006.01) |
| *G16H 20/30* | (2018.01) |

(Continued)

(52) U.S. Cl.
CPC ...... *A63B 71/0622* (2013.01); *A63B 24/0003* (2013.01); *A63B 60/46* (2015.10); *A63B 71/0669* (2013.01); *G06N 3/08* (2013.01); *G16H 20/30* (2018.01); *A63B 69/36* (2013.01); *A63B 2069/3602* (2013.01); *A63B 2071/0691* (2013.01); *A63B 2102/32* (2015.10); *A63B 2220/12* (2013.01); *A63B 2220/51* (2013.01); *A63B 2220/56* (2013.01); *A63B 2220/72* (2013.01); *A63B 2220/74* (2013.01); *A63B 2220/75* (2013.01); *A63B 2220/76* (2013.01); *A63B 2220/803* (2013.01); *A63B 2220/807* (2013.01); *A63B 2220/808* (2013.01); *A63B 2220/833* (2013.01); *A63B 2220/836* (2013.01); *A63B 2225/50* (2013.01); *A63B 2230/06* (2013.01); *A63B 2230/202* (2013.01);

(Continued)

(58) Field of Classification Search
USPC .................................................. 473/223, 407
See application file for complete search history.

(56) References Cited

U.S. PATENT DOCUMENTS

| | | |
|---|---|---|
| 5,507,485 A | 4/1996 | Fisher |
| 5,528,248 A | 6/1996 | Steiner et al. |

(Continued)

OTHER PUBLICATIONS

U.S. Appl. No. 15/312,500, filed Nov. 18, 2016, US 2017-0087431 A1.

(Continued)

*Primary Examiner* — Pierre E Elisca
(74) *Attorney, Agent, or Firm* — McCarter & English, LLP

(57) ABSTRACT

Exemplary embodiments of the present disclosure are directed to systems, methods, and computer-readable media configured to autonomously generate personalized recommendations for a user before, during, or after a round of golf. The systems and methods can utilize course data, environmental data, user data, and/or equipment data in conjunctions with one or more machine learning algorithms to autonomously generate the personalized recommendations.

23 Claims, 12 Drawing Sheets

(51) Int. Cl.
　　　*A63B 69/36*　　　　(2006.01)
　　　*A63B 102/32*　　　(2015.01)
　　　*G06N 20/00*　　　　(2019.01)
(52) U.S. Cl.
　　　CPC ..... *A63B 2230/207* (2013.01); *A63B 2230/30* (2013.01); *A63B 2230/50* (2013.01); *G06N 20/00* (2019.01)

(56) References Cited

U.S. PATENT DOCUMENTS

| | | | |
|---|---|---|---|
| 5,565,845 A | 10/1996 | Hara | |
| 5,685,786 A | 11/1997 | Dudley | |
| 5,699,244 A | 12/1997 | Clark, Jr. et al. | |
| 5,740,077 A | 4/1998 | Reeves | |
| 5,966,135 A | 10/1999 | Roy et al. | |
| 6,024,655 A | 2/2000 | Coffee et al. | |
| 6,045,364 A | 4/2000 | Dugan et al. | |
| 6,118,376 A | 11/2000 | Regester | |
| 6,261,102 B1 | 7/2001 | Dugan et al. | |
| 6,282,362 B1 | 8/2001 | Murphy et al. | |
| 6,299,553 B1 | 10/2001 | Petuchowski | |
| 6,324,473 B1 | 11/2001 | Eschenbach | |
| 6,366,205 B1 | 4/2002 | Sutphen | |
| 6,441,745 B1 | 8/2002 | Gates | |
| 6,456,938 B1 | 9/2002 | Barnard | |
| 6,520,864 B1 | 2/2003 | Wilk | |
| 6,537,076 B2 | 3/2003 | McNitt et al. | |
| 6,582,328 B2 | 6/2003 | Kuta et al. | |
| 6,697,820 B1 | 2/2004 | Tarlie | |
| 6,753,778 B2 | 6/2004 | Kruger | |
| 6,905,339 B2 | 6/2005 | DiMare et al. | |
| 7,010,550 B2 | 3/2006 | Tarlie | |
| 7,118,498 B2 | 10/2006 | Meadows et al. | |
| 7,121,962 B2 | 10/2006 | Reeves | |
| 7,254,516 B2 | 8/2007 | Case et al. | |
| 7,264,554 B2 | 9/2007 | Bentley | |
| 7,603,255 B2 | 10/2009 | Case et al. | |
| 7,800,480 B1 | 9/2010 | Balardeta et al. | |
| 7,801,575 B1 | 9/2010 | Balardeta et al. | |
| 7,804,404 B1 | 9/2010 | Balardeta et al. | |
| 7,831,212 B1 | 11/2010 | Balardeta et al. | |
| 7,847,693 B1 | 12/2010 | Balardeta et al. | |
| 7,853,211 B1 | 12/2010 | Balardeta et al. | |
| 7,883,427 B1 | 2/2011 | Balardeta et al. | |
| 7,883,428 B1 | 2/2011 | Balardeta et al. | |
| 7,894,286 B2 | 2/2011 | Jung et al. | |
| 7,899,408 B1 | 3/2011 | Balardeta et al. | |
| 7,911,186 B1 | 3/2011 | Balardeta et al. | |
| 7,915,865 B1 | 3/2011 | Balardeta et al. | |
| 7,922,606 B2 | 4/2011 | Balardeta et al. | |
| 7,927,225 B1 | 4/2011 | Balardeta et al. | |
| 7,941,097 B1 | 5/2011 | Balardeta et al. | |
| 7,942,762 B2 | 5/2011 | Balardeta et al. | |
| 7,946,926 B1 | 5/2011 | Balardeta et al. | |
| 7,979,030 B1 | 7/2011 | Balardeta et al. | |
| 8,016,690 B2 | 9/2011 | Rushe | |
| 8,070,628 B2 | 12/2011 | Denton et al. | |
| 8,113,967 B1 | 2/2012 | Seluga et al. | |
| 8,120,332 B2 | 2/2012 | Balardeta et al. | |
| 8,137,208 B2 | 3/2012 | Ahem et al. | |
| 8,142,302 B2 | 3/2012 | Balardeta et al. | |
| 8,142,304 B2 | 3/2012 | Reeves | |
| 8,147,335 B2 | 4/2012 | Kim et al. | |
| D659,787 S | 5/2012 | Balardeta et al. | |
| 8,172,702 B2 | 5/2012 | Meadows et al. | |
| 8,192,293 B2 | 6/2012 | Denton et al. | |
| 8,202,148 B2 | 6/2012 | Young | |
| 8,210,959 B2 | 7/2012 | Balardeta et al. | |
| 8,221,269 B2 | 7/2012 | Meadows et al. | |
| 8,226,495 B2 | 7/2012 | Savarese et al. | |
| 8,272,970 B2 | 9/2012 | Balardeta et al. | |
| 8,337,335 B2 | 12/2012 | Dugan | |
| 8,355,869 B2 | 1/2013 | Balardeta et al. | |
| 8,364,293 B2 | 1/2013 | Doherty et al. | |
| 8,409,024 B2 | 4/2013 | Marty et al. | |
| 8,430,762 B2 | 4/2013 | Balardeta et al. | |
| 8,430,770 B2 | 4/2013 | Dugan | |
| 8,444,499 B2 | 5/2013 | Balardeta et al. | |
| 8,446,255 B2 | 5/2013 | Balardeta et al. | |
| 8,460,111 B2 | 6/2013 | Hart | |
| 8,465,376 B2 | 6/2013 | Bentley | |
| 8,523,711 B2 | 9/2013 | Meadows et al. | |
| 8,529,380 B1 | 9/2013 | Hubenthal et al. | |
| 8,535,170 B2 | 9/2013 | Reeves | |
| 8,556,752 B2 | 10/2013 | Meadows et al. | |
| 8,620,463 B2 | 12/2013 | Doherty et al. | |
| 8,624,738 B2 | 1/2014 | Savarese et al. | |
| 8,647,214 B2 | 2/2014 | Wiegers | |
| 8,655,462 B2 | 2/2014 | Sanders | |
| 8,668,595 B2 | 3/2014 | Boyd et al. | |
| 8,696,482 B1 | 4/2014 | Pedenko et al. | |
| 8,708,841 B2 | 4/2014 | Doherty et al. | |
| 8,758,152 B2 | 6/2014 | Hall | |
| 8,758,170 B2 | 6/2014 | Reeves | |
| 8,764,576 B2 | 7/2014 | Takasugi | |
| 8,808,102 B2 | 8/2014 | Dugan | |
| 8,808,114 B2 | 8/2014 | Dugan | |
| 8,831,905 B2 | 9/2014 | Papadourakis | |
| 8,840,483 B1 | 9/2014 | Steusloff et al. | |
| 8,840,484 B2 | 9/2014 | Parke et al. | |
| 8,845,459 B2 | 9/2014 | Balardeta et al. | |
| 8,870,673 B2 | 10/2014 | Beno et al. | |
| 8,894,502 B2 | 11/2014 | Rose | |
| 8,926,445 B2 | 1/2015 | Davenport | |
| 8,933,967 B2 | 1/2015 | Huston et al. | |
| 8,979,665 B1 | 3/2015 | Najafi et al. | |
| 8,986,129 B2 | 3/2015 | Miettinen et al. | |
| 8,986,130 B2 | 3/2015 | Hatton et al. | |
| 8,989,441 B2 | 3/2015 | Han et al. | |
| 9,005,047 B2 | 4/2015 | Savarese et al. | |
| 9,022,870 B2 | 5/2015 | Jeffery et al. | |
| 9,050,519 B1 | 6/2015 | Ehlers et al. | |
| 9,095,761 B2 | 8/2015 | Trenkle et al. | |
| 9,186,546 B2 | 11/2015 | Boyd et al. | |
| 9,199,177 B2 | 12/2015 | Knapp et al. | |
| 9,375,624 B2 | 6/2016 | Boyd et al. | |
| 9,393,478 B2 | 7/2016 | Niegowski | |
| 9,403,072 B2 | 8/2016 | Baker et al. | |
| 9,403,073 B2 | 8/2016 | McDonnell et al. | |
| 9,409,071 B1 | 8/2016 | Beno et al. | |
| 9,433,844 B2 | 9/2016 | Boyd et al. | |
| 9,535,162 B2 | 1/2017 | Park | |
| 9,630,079 B2 | 4/2017 | Davenport | |
| 9,646,199 B2 | 5/2017 | Bose et al. | |
| 9,649,532 B2 | 5/2017 | Case | |
| 9,656,134 B2 | 5/2017 | Meadows et al. | |
| 9,656,147 B2 | 5/2017 | Reeves | |
| 9,731,182 B2 | 8/2017 | Dugan | |
| 9,770,639 B2 | 9/2017 | Blanc | |
| 9,789,361 B2 | 10/2017 | Beno et al. | |
| 9,916,001 B2 | 3/2018 | Thurman et al. | |
| 9,925,439 B2 | 3/2018 | Baker et al. | |
| 9,943,744 B2 | 4/2018 | Meadows et al. | |
| 9,968,826 B2 | 5/2018 | McDonnell et al. | |
| 9,968,827 B2 | 5/2018 | Beno et al. | |
| 2002/0115047 A1 | 8/2002 | McNitt et al. | |
| 2002/0188359 A1 | 12/2002 | Morse | |
| 2004/0121849 A1 | 6/2004 | Curkovic et al. | |
| 2005/0032582 A1 | 2/2005 | Mahajan et al. | |
| 2005/0227791 A1 | 10/2005 | McCreary et al. | |
| 2006/0148594 A1 | 7/2006 | Saintoyant et al. | |
| 2006/0178110 A1 | 8/2006 | Nurminen et al. | |
| 2007/0129178 A1 | 6/2007 | Reeves | |
| 2009/0017944 A1 | 1/2009 | Savarese et al. | |
| 2009/0209358 A1 | 8/2009 | Niegowski | |
| 2010/0149331 A1 | 6/2010 | DiMare et al. | |
| 2011/0230986 A1 | 9/2011 | Lafortune et al. | |
| 2011/0281670 A1 | 11/2011 | Balardeta | |
| 2011/0301435 A1 | 12/2011 | Albert et al. | |
| 2012/0004956 A1 | 1/2012 | Huston et al. | |
| 2012/0088544 A1 | 4/2012 | Bentley et al. | |
| 2012/0238381 A1 | 9/2012 | Denton et al. | |
| 2012/0289354 A1 | 11/2012 | Cottam et al. | |

(56) References Cited

U.S. PATENT DOCUMENTS

| | | |
|---|---|---|
| 2012/0322569 A1 | 12/2012 | Cottam |
| 2013/0095939 A1 | 4/2013 | Meadows et al. |
| 2013/0095989 A1 | 4/2013 | Eichler et al. |
| 2013/0144411 A1 | 6/2013 | Savarese et al. |
| 2013/0150121 A1 | 6/2013 | Jeffery et al. |
| 2013/0267335 A1 | 10/2013 | Boyd |
| 2013/0267336 A1 | 10/2013 | Boyd et al. |
| 2014/0018181 A1 | 1/2014 | Blake et al. |
| 2014/0018195 A1 | 1/2014 | Meadows et al. |
| 2014/0172132 A1 | 6/2014 | Ura |
| 2014/0221118 A1 | 8/2014 | Meadows et al. |
| 2014/0244012 A1 | 8/2014 | Doherty et al. |
| 2014/0274240 A1 | 9/2014 | Meadows |
| 2014/0277630 A1 | 9/2014 | Meadows et al. |
| 2014/0278207 A1 | 9/2014 | Hadden et al. |
| 2014/0315660 A1 | 10/2014 | Edmonson et al. |
| 2014/0336989 A1 | 11/2014 | Ye et al. |
| 2015/0068616 A1 | 3/2015 | Early et al. |
| 2015/0080011 A1 | 3/2015 | Zelinka et al. |
| 2015/0100245 A1 | 4/2015 | Huang et al. |
| 2015/0105172 A1 | 4/2015 | Thurman et al. |
| 2015/0141005 A1 | 5/2015 | Suryavanshi et al. |
| 2015/0317801 A1* | 11/2015 | Bentley ............... H04N 7/181 382/107 |
| 2016/0292509 A1* | 10/2016 | Kaps ............... G06K 9/00718 |
| 2017/0216705 A1 | 4/2017 | Reeves |
| 2017/0262697 A1* | 9/2017 | Kaps ............... A63F 13/812 |
| 2017/0272703 A1* | 9/2017 | Allen ............... G06Q 10/0639 |

OTHER PUBLICATIONS

U.S. Appl. No. 15/714,235, filed Sep. 25, 2017, US 2018-0015349 A1.

\* cited by examiner

US 10,682,562 B2

AUTONOMOUS PERSONALIZED GOLF RECOMMENDATION AND ANALYSIS ENVIRONMENT

CROSS-REFERENCE TO RELATED APPLICATIONS

The present application claims priority benefit to U.S. Provisional Application No. 62/447,221, entitled "Autonomous Personalized Golf Recommendation and Analysis Environment," which was filed on Jan. 17, 2017. The content of the foregoing provisional application is hereby incorporated by reference.

BACKGROUND

In recent years, there has been efforts to monitor, track, and/or analyze a golfer's performance during a round of golf using one or more sensors associated with the golfer or the golf clubs. While this technology continues to advance and enhance golfer performance, there remains a need for additional improvements to aid golfers and enhance performance.

SUMMARY

Exemplary embodiments of the present disclosure are directed to various components of systems, methods, and/or non-transitory computer-readable media that facilitate autonomous personalized recommendations and analysis of a user's golf game based on one or more parameters or data sets. One or more machine learning algorithms can be utilized to provide outputs personalized to a specific user. For example, personalize recommendations can be autonomously generated by embodiments of the present disclosure before, during, and/or after a user engages in a round of golf.

In accordance with embodiments of the present disclosure, a method of autonomously generating personalized recommendations for a user before, during, or after a round of golf is disclosed. The method includes receiving an input from a user associated with a round of golf; retrieving course data, environmental data, user data, and/or equipment data from one or more sensors and data sources; autonomously generating a recommendation or analysis for the user based on the course data, the environment data, the user data, and/or the equipment data in response to executing of one or more machine learning algorithms that consume the course data, the environmental data, the user data, and/or the equipment data; and outputting the recommendation or analysis to the user.

In accordance with embodiments of the present disclosure, a system for autonomously generating personalized recommendations for a user before, during, or after a round of golf is disclosed. The system includes one or more computer-readable media storing course data, environmental data, user data, and/or equipment data. The system also includes one or more servers configured to: receive an input from a user associated with a round of golf; retrieve the course data, the environmental data, the user data, and/or the equipment data from one or more computer-readable media; autonomously generate a recommendation or analysis for the user based on the course data, the environment data, the user data, and/or the equipment data in response to executing of one or more machine learning algorithms that consume the course data, the environmental data, the user data, and the equipment data; and output the recommendation or analysis to the user.

Any combination and/or permutation of embodiments is envisioned. Other embodiments, objects, and features will become apparent from the following detailed description considered in conjunction with the accompanying drawings. It is to be understood, however, that the drawings are designed as an illustration only and not as a definition of the limits of the present disclosure.

DETAILED DESCRIPTION

Exemplary embodiments of the present disclosure are directed to various components of systems, methods, and non-transitory computer-readable media for automatic performance tracking of a round of golf and autonomous personalize recommendations and analysis based on machine learning using the automatic performance tracking and a large corpus of data points (e.g., millions) associated with user data, environmental data, equipment data, course data, and the like. The recommendations and/or analysis can be autonomously provided on a hole-by-hole and/or shot-by-shot basis before, during, and/or after a round of golf. The recommendations and/or analysis can utilize a user's personal performance history, golf shot data collected by the sensors associated with a plurality of users, weather conditions, elevation, golf course features, equipment selections, and the like.

In accordance with embodiments of the present disclosure, the user data, environmental data, equipment data, and/or course data can be obtained from one or more data sources and/or sources, and/or can be measured via one or more sensors. As one example, in some embodiments, user data and/or equipment data can be automatically monitored and/or tracked during a round of golf using one or more sensor modules associated with the user/golfer and/or golf clubs being used by the user/golfer. Embodiments can include sensor modules configured to be secured or fixed to golf clubs (e.g., embedded or integrated into the grip of a golf club), can be included in one or more modules carried or worn by the user/golfer, and/or can be both secured or fixed to a golf clubs and can be included in modules carried or worn by the user/golfer. As another example, environmental sensors can be distributed at golf courses to measure environmental properties over time, such as humidity, wind speed, precipitation levels, sun angles, ambient light level, and the like. The data measured by the one or more sensors (e.g., disposed at the golf courses, affixed to/embedded in the golf clubs, and/or carried or worn by the users can be transmitted, directly or indirectly, to one or more remote servers to be stored in one or more databases and/or to be utilized to facilitate autonomous personalized recommendations and analysis of the users' golf games.

Figure 1:
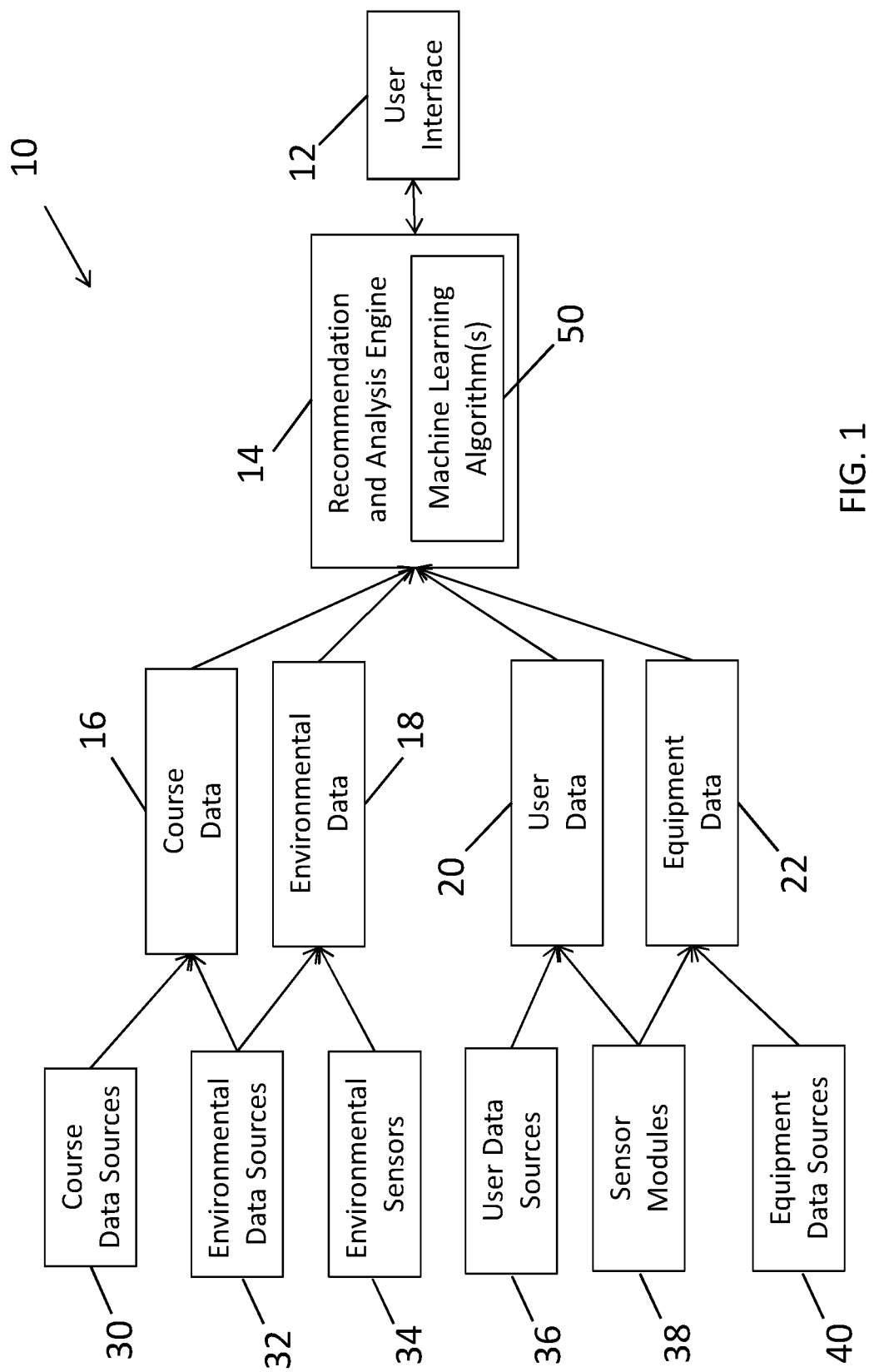
FIG. 1 is an autonomous golf recommendation and analysis environment in accordance with embodiments of the present disclosure.

FIG. 1 is an autonomous golf recommendation and analysis environment 10 in accordance with embodiments of the present disclosure. The environment 10 can be configured to provide autonomous, dynamic, and real-time recommendations and analysis to users, and can include a user interface 12, a recommendation and analysis engine 14, and at least one of course data 16, environmental data 18, user data 20, and/or equipment data 22. The environment 10 can be responsive to user input received via the user interface to generate one or more recommendations and/or analytical data based on the data 16, 18, 20, and 22.

The course data 16 can be received via one or more course data sources 30 and/or can be measured by one or more environmental sensors 32 at one or more golf courses. The course data 16 can include, but is not limited to golf course data, such as course features, course ground conditions, type of grass (fairway/rough/green), length of rough, green speed, number of tee boxes, size of tee boxes, number of hazards, size of hazards, type of green, size of greens, location of hazards relative to fairway and green, type of sand in bunker, depth of bunkers, elevation changes on course, pace of play, pin positions, geographic location, altitude of course, number of trees, types of trees, other vegetation, topography (desert/park land/seaside, etc), accessibility (e.g., public vs. private vs. resort), presence of caddies, course rating (golf advisor/yelp/etc.), course architect, course architectural style, frequency of mowing, schedule of mowing, mowing pattern, frequency of green rolling, schedule of green rolling, frequency of watering, schedule of watering, watering pattern, heat map of course usage, total yardage, order of pars (i.e. 4,4,5,4,3 . . . ), number of each par, length of holes, length of OB, topography of greens, initiation fees/dues, metal spikes (e.g., allowed, not allowed), practice range present at course, practice green present at course, practice bunker present, practice chipping area, number of rounds played per year, and/or beer cart present/frequency.

The environmental data 18 can be measured by one or more environmental sensors 32 at or in geographic proximity to one or more golf courses (e.g., one or more local or regional weather monitoring stations) and/or can be received via one or more course data sources 34. The environmental data 18 can include, but is not limited to wind speed, wind direction, temperature, humidity, barometric pressure, previous weather conditions (e.g., the previous day, week, month) including for example precipitation influencing ground conditions, luminosity, length of day, sun angle, time of sunset, time of sunrise, shadows, solar reflection, and/or time of year The user data 20 can be received via one or more user data sources 36 and/or can be measured by one or more sensors 38 carried or worn by users during a round of golf and/or one or more sensors affixed to or embedded in one or more golf clubs. As one example, the sensors 38 can include one or more sensors disposed in a user's shoes, in a wristband or watch worn by the user, in a user's pocket, on/in a user's belt, in a glove worn by the user, in a user's glasses, in a shaft of a golf club, in a grip of a golf club, in a head of a golf club, and the like. The sensors 38 can include inertial sensors, such as accelerometers and gyroscopes; force sensors, such as pressure sensors, strain gauges, piezoelectric sensors; blood pressure sensors; blood sugar sensors; pulse oximeter sensors; heart rate sensors; temperature sensors; moisture sensors; light sensors; acoustic transducers, such as microphones; chemical sensors; and/or any suitable type of sensor.

The user data 20 can include, but is not limited to golfer data, such as age, gender, weight, height, golf handicap, strokes gained by facet, years golfing, frequency with which a user plays a round of golf, nationality, race, religion, sexual orientation, hydration level, fitness level, resting heart rate, blood pressure, glucose levels, medications, stress level, flexibility, percentage body fat, hip rotation, body type, apparel, swing plane, putting grip, golf grip, other sports played, lowest score, variance of scores, relationship status, number of children, average sleep per night, alcohol consumption, illicit drug usage, occupation, industry of employment, whether the user has played in amateur tournaments, whether the user has played in professional tournaments, chronic diseases, injuries, eye sight, calorie intake, handedness (right/left), IQ, club distances, trend lines (trending longer/more accurate golf shots, etc), social data (e.g., quantity of Facebook friends, quantity of twitter followers, frequency of social media usage), ability to handle pressure as measured by past performance in "pressure" situations, data from golf simulators (such as Trackman and Foresight), and/or who the user's golf instructor is.

The user data 20 can include golf round data and golf shot data, such as fatigue level during round, playing partners, type of golf game played (scramble, best ball etc.), start time of round, type of round (tournament/pleasure), score, swing tempo, swing speed, swing plane, type of club, type of shot (full/half), ball flight path (draw/fade/low/high, etc), length of shot, length of intended shot, location of start of shot, location of end of shot, hole/course shot is on, type of stance, performance of previous shots, raw or processed sensor data during a golf shot (e.g., gyroscope data, accelerometer data, magnetometer data, microphone data, GPS data, proximity sensor data, force sensor data) from sensors in or on wrist bands, watch, portable electronic devices, belts, gloves, golf club shafts, golf club grips, golf club heads, shoes, glasses, and the like.

The user data 20 can also include historical player performance data, such as percent of Eagles, percent of Birdies, percent of Pars, percent of Bogeys, percent of Double Bogeys, percent of greater than Double Bogeys, drive distances, longest drives, percent of fairways hit, percent of left of fairway, percent of right of fairway, greens in regulation, distance to pin on greens hit in regulation distance to pin on all approaches, percent of greens missed short, percent of greens missed left, percent of greens missed right, percent of greens missed long, Chip & Down percentage, average distance to pin after chip, Sand & Down percentage, Sand Save percentage, average distance to pin after sand shot, putts per hole, putts per GIR, one putt percentage, two putt percentage, three putt percentage, strokes gained driving, strokes gained approach, strokes gained layup, strokes gained chipping, strokes gained sand, strokes gained putting, fairway bunker percentage, greenside bunker percentage, tee OB percentage, approach OB percentage, fairway water hazard percentage, green water hazard percentage, average putts segmented by approach distance, and so on.

The equipment data 22 can be measured by one or more sensors 38 carried or worn by users during a round of golf and/or one or more sensors affixed to or embedded in one or more golf clubs and/or can be received via one or more user data sources 40. The equipment data 22 can include, but is not limited to equipment attributes, such as brand of each club, brand of putter, brand of ball, brand of shoes, brand of glove, brand of hat, all apparel brands, shaft bend, shaft stiffness, shaft length per club, grip brand, grip size, club lie angle, club loft, driver/wood configuration (draw/slice biased, loft angle), GPS device used, driver head size, year of each club, number of shots take with each club, golf bag brand, golf bag type (carry/cart), and golf bag weight.

The equipment data 22 can also include historical per club performance data, such as, for example, percent of Eagles with club off of tee, percent of Birdies with club off of tee, percent of Pars with club off of tee, percent of Bogeys with club off of tee, percent of Double Bogeys with club off of tee, percent of Eagles with club on approach, percent of Birdies with club on approach, percent of Pars with dub on approach, percent of Bogeys with club on approach, percent of Double Bogeys with club on approach, percent of greater than Double Bogeys with club on approach, drive distances, longest drive, percent of fairways hit, percent of left of fairway, percent of right of fairway, greens in regulation, distance to pin on greens hit in regulation, distance to pin on all approaches, percent of greens missed short, percent of greens missed left, percent of greens missed right, percent of greens missed long, Chip & Down percentage, average distance to pin after chip, Sand & Down percentage, Sand Save percentage, average distance to pin after sand shot, putts per hole after using club on approach, putts per GU after using club on approach, one putt % after using club on approach, two putt percentage after using club on approach, three or more putt percentage after using club on approach, strokes gained driving with club, strokes gained approach with club, strokes gained layup with club, strokes gained chipping with club, strokes gained sand with club, strokes gained putting with club fairway bunker percentage with club, greenside bunker percentage with club, tee OB percentage with club, approach OB percentage with club, fairway water hazard percentage with club, green water hazard percentage with club, total shots with club, last time club was used, longest distance achieved by the club, average distance for the club, smart distance for the club, variance for the club, and/or percent of "bad" shots hit by the club.

The user interface 12 can provide one or more graphical user interfaces and/or one or more application-program interfaces (APIs) that can be access and/or utilized by a user to interact with environment 10. The user interface 12 can receive text input and/or speech input. The user interface 12 can employ natural language processing and/or speech recognition techniques to process user input received via the user interface 12. In exemplary embodiments, the user can access the environment via a user device configured to communicate with remote device via a communications network. In some instance the user interface or portions thereof can be installed on the user device such that the environment 10 can be implemented in a distributed manner. In some instances, the user device can include an application, such as a web browser or specially configured application associated with the environment 10. The user device can interact with the user interface 12 to allow the user of the user device to receive dynamic, real-time golf recommendations and analyses before, during, and/or after a round of golf. The golf recommendations and analyses can be generated in response to data 16, 18, 20, and 22 that has previously been measured and received and/or that is contemporaneously measured and received and/or can be generated in response to receipt of user input. For example, in embodiments of the present disclosure, the user may interface with the environment via the user interface 12 to ask a question, such as "which club should I use for this shot?", "what should my strategy be for playing this golf course?", or "what can I do to improve my score the next time I play this golf course?"

The engine 14 can receive requests from the user interface 12 and receive the data 16, 18, 20, and/or 22 to generate golf recommendations and analyses. Exemplary embodiments of the engine 14 can include one or more machine learning algorithms 50 configured to process the data 16, 18, 20, and/or 22. As one example, the engine 14 can execute one or more of the machine learning algorithms 50 to provide post-round analysis of a user's round of golf to generate one or more personalized recommendations or analyses identifying strategies and/or areas where the user can improve the user's golf game. As another example, the engine 14 can execute one or more of the machine learning algorithms 50 to provide pre-round analysis for a golf course the user intends to play to generate one or more personalized recommendations or analyses identifying strategies for playing the golf course. As another example, the engine 14 can execute the one or more machine learning algorithms 50 to provide personalized hole-by-hole and/or shot-by-shot recommendations or analyses identifying strategies for playing a hole or shot.

In exemplary embodiments, the one or more machine learning algorithms 50 can include, for example, supervised learning algorithms, unsupervised learning algorithm, artificial neural network algorithms, artificial neural network algorithms, association rule learning algorithms, hierarchical clustering algorithms, cluster analysis algorithms, outlier detection algorithms, semi-supervised learning algorithms, reinforcement learning algorithms and/or deep learning algorithms Examples of supervised learning algorithms can include, for example, AODE; Artificial neural network, such as Backpropagation, Autoencoders, Hopfield networks, Boltzmann machines, Restricted Boltzmann Machines, and/or Spiking neural networks; Bayesian statistics, such as Bayesian network and/or Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor algorithms and/or Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and/or Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, and/or Support vector machines; Quadratic classifiers; k-nearest neighbor; Boosting; Decision trees, such as C4.5, Random forests, ID3, CART, SLIQ, and/or SPRINT; Bayesian networks, such as Naive Bayes; and/or Hidden Markov models. Examples of unsupervised learning algorithms can include Expectation-maximization algorithm; Vector Quantization; Generative topographic map; and/or Information bottleneck method. Examples of artificial neural network can include Self-organizing maps. Examples of association rule learning algorithms can include Apriori algorithm; Eclat algorithm; and/or FP-growth algorithm. Examples of hierarchical clustering can include Single-linkage clustering and/or Conceptual clustering. Examples of cluster analysis can include K-means algorithm; Fuzzy clustering; DBSCAN; and/or OPTICS algorithm. Examples of outlier detection can include Local Outlier Factors. Examples of semi-supervised learning algorithms can include Generative models; Low-density separation; Graph-based methods; and/or Co-training. Examples of reinforcement learning algorithms can include Temporal difference learning; Q-learning; Learning Automata; and/or SARSA. Examples of deep learning algorithms can include Deep belief networks; Deep Boltzmann machines; Deep Convolutional neural networks; Deep Recurrent neural networks; and/or Hierarchical temporal memory.

The engine 14 can execute a combination of the machine learning algorithms 50 in sequence and/or concurrently with one another to generate the personalized recommendations or analyses. As one example, the engine 14 can execute two or more machine learning algorithms 50 concurrently with one another such that each of the machine learning algorithms 50 being executed generates an output based on the data 16, 18, 20, and/or 22 and received user input. The engine 14 can weight the outputs of the machine learning algorithms such that the outputs of the machine learning algorithms 50 can be prioritized or ranked and may be combined to arrive at a personalized recommendation or analysis. The engine 14 can use a voting model in which the outputs of each of the machine learning algorithms 50 can count as a vote and the recommendation or analysis with the most votes is chosen by the engine 14 and output to the user via the user interface 12. In some embodiments, the weighting employed by the engine 14 can give different numbers of votes to different machine learning algorithms. In some embodiments, the engine 14 can dynamically adjust the weighting and/or voting model based on whether the generated personalized recommendation or analysis chosen by the engine 14 and output to the user achieved an intended result.

Figure 2:
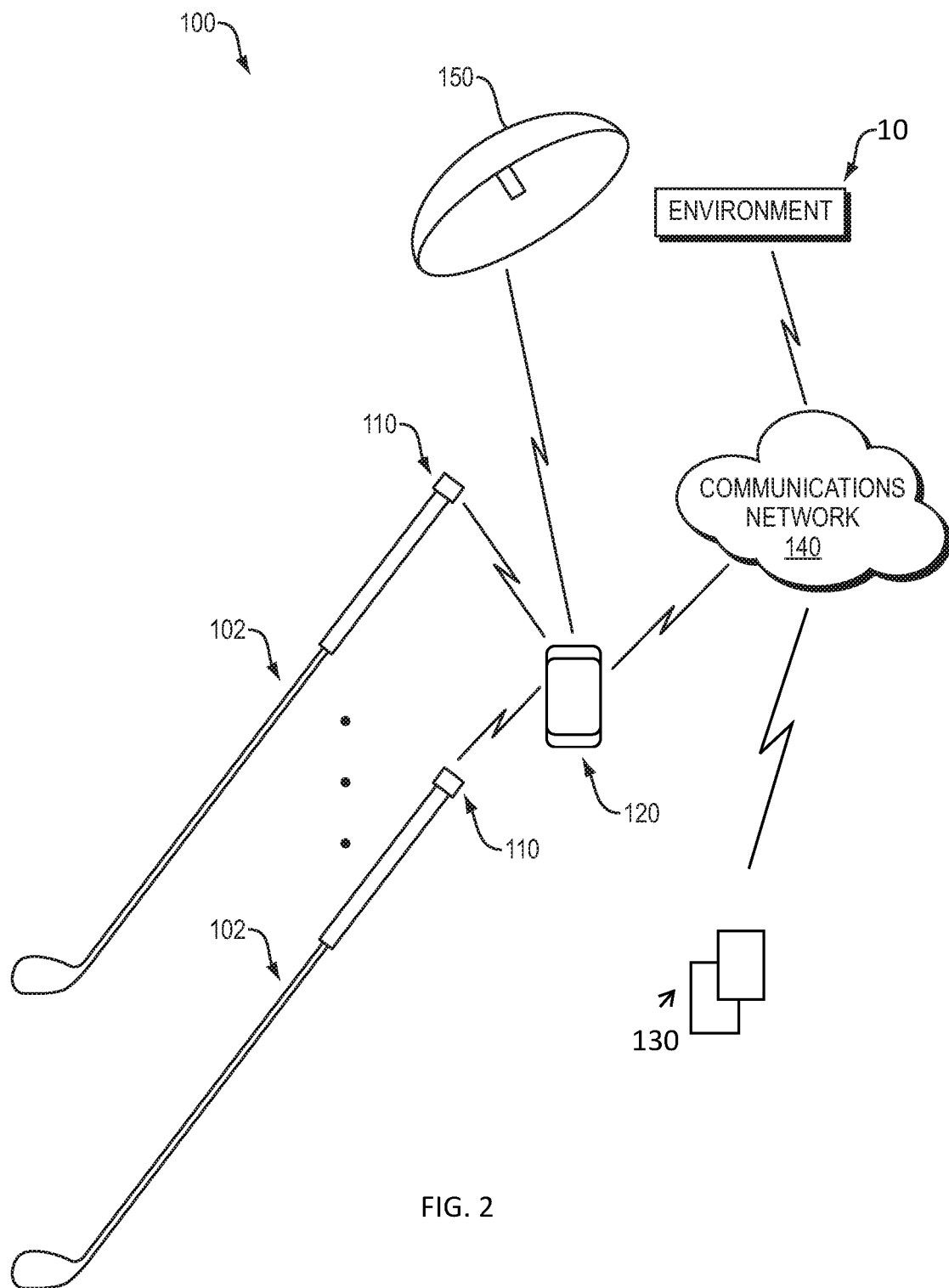
FIG. 2 depicts a performance monitoring and recommendation system in accordance with exemplary embodiments of the present disclosure.

FIG. 2 depicts an exemplary system 100 that can be implemented using hardware, software, and/or a combination thereof to facilitate personalized recommendations or analysis by embodiments of the environment 10. The system 100 can track and/or analyze user performance associated with a user and golf clubs 102 of the user. The system 100 can include sensor modules 110 secured or fixed to the golf clubs 102 and electronic devices 120 (e.g., mobile phones, tablets, laptops, wristbands, watches, shoes, belts, etc.) that are configured to communicate with one or more of the sensor modules 110. In some embodiments, the system 100 can include the environment 10 that can be accessible by users via a communications network 140 as described in more detail herein to facilitate personalized recommendations or analyses.

In exemplary embodiments, the sensor modules 110 and/or electronic devices 120 can detect when a user is preparing to swing a respective one of the golf clubs 102, can detect when the golf club is being swung, and/or can detect when the golf club strikes an object. The sensor module 110 and/or electronic devices 120 can use this information to compute and/or identify performance characteristics associated with the user's use of the golf clubs 102. For embodiments in which the sensor modules compute and/or identify the performance characteristics related to the swing, the sensor modules 110 can transmit the performance characteristics, direct or indirectly, to one or more of the electronic devices 120 and/or to the environment 10. As one example, in some embodiments, the sensor modules 110 can detect and/or identify performance characteristics including when the golf clubs 102 are swung, acceleration information associated with the swing, whether the golf club hits another object, and/or whether the swing and impact correspond to a swing that should be counted as a shot (e.g., a golf shot), and can transmit a message to the electronic device(s) including the performance characteristics.

Each sensor module 110 can be associated with a unique identifier. The unique identifier can be included in transmissions by the sensor modules 110 and can be used by the one or more electronic devices 120 and/or the environment 10 to associate the transmissions with the corresponding golf clubs 102. In exemplary embodiments, the unique identifier can be a sequence or string of alphanumeric characters.

The one or more electronic devices 120 can sense or receive the performance characteristics and can use the performance characteristics to monitor and/or track the user's performance during a round of golf, and to render one or more graphical user interfaces to display the performance characteristics as well as other data maintained, generated, and/or received by the one or more electronic devices 120. For example, the one or more electronic devices 120 can be programmed and/or configured to identify a location of the user when one of the golf clubs 102 is swung and/or contacts an object (e.g., a ball, the ground, or any other object) during a swing, which can be transmitted to the environment 10, and the environment 10 can use the location information to determine where the user is golfing, a hole the user is on, and can be used by the environment to retrieve and/or measure course data, environmental data, user data, and equipment data. In exemplary embodiments, the location of the electronic devices 120 (e.g., a longitude and latitude) can be determined using a global positioning system (GPS) receiver within the electronic devices 120 that is in communication with a GPS satellite 150.

In exemplary embodiments, the one or more electronic devices 120 can be programmed and/or configured to associate the unique identifiers of each of the sensor modules 110 with a corresponding one of the golf clubs 102 such that when the one or more electronic devices 120 receives a transmission from one of the sensor modules 110, the one or more electronic devices 120 can determine which of the golf clubs was used to generate the information included in the transmission (e.g., performance characteristics). For example, in exemplary embodiments, the sensor modules 110 and the electronic device(s) 120 can be configured to be associated such that each of the sensor modules 110 can be recognized and/or paired with the one or more electronic devices 120. During a formation or pairing process, each sensor module 110 can send its unique identifier to the one or more electronic devices 120 and the user(s) can interact with the one or more electronic devices to identify the corresponding golf clubs 102 to which each of the sensor modules 110 are secured/attached. The electronic devices 120 can store this information for use when it receives subsequent transmissions from the sensor modules 110. In exemplary embodiments, the sensor modules 110 and the electronic device(s) 120 can transmit and/or receive wireless transmissions according to the BlueTooth® communication protocol, Zigbee® communication protocol, the Wi-Fi® communication protocol, and/or any other suitable communication protocols.

The environment 10 can be implemented by a remote system that includes one or more computing devices operating as servers to manage data/information regarding a user's profile, account, performance, user data, course data, environment data, equipment data, and/or any other data/information associated with users of the environment 10. In exemplary embodiments, the electronic device(s) 120 can communicate with the environment 10 to transmit and receive information (e.g., via the user interface 12 shown in FIG. 1). As one example, the environment 10 can be programmed and/or configured to receive user performance information from the electronic device(s) 120 and to process and/or analyze the performance information to determine statistics regarding the users performance, to provide an analysis regarding a user's mechanics (e.g., a swing analysis), and/or to provide personalized recommendations or analyses before, during, or after a round of golf. Some non-limiting examples of statistics and swing analysis information that can be determined by the environment 10 can include a swing tempo, swing velocity, swing force, club face angle, swing plane, and/or impact force with which the golf club strikes or will strike an object, and/or any other swing parameters as well as club consistency (e.g., variations in shot distances), putting stats (e.g., average putts per hole, 2- putt percentage, 3+ putt-percentage, 1 putt per round, etc.), scrambling statistics (e.g., the golfer's ability to get par when hitting the green in regulation is missed), sand saves (e.g., the ability of a golfer to get par when the ball lands in a bunker during a hole), fairway hits (e.g., percentage of times a golfer hits the fairway when the golf ball is hit from the tee), and the like, as well as other user data or equipment data as described herein.

Subsequent to determining the statistics and/or providing the analysis, the environment 10 can transmit the statistics, personalized recommendations and/or analyses to the electronic devices 120, which can be programmed to display the statistics, personalized recommendations and/or analyses to the users. The environment 10 can transmit the golf course data to the electronic devices 120 upon request and/or can transmit the golf course data automatically (e.g., based on the location of the user). The golf course data can allow the electronic devices 120 to display the golf course data to the users, use the golf course data for automatically determining a user's performance on a golf course, and/or overlay the users performance on the golf course data rendered on a display.

In one exemplary embodiment, the system 100 can be implemented to monitor and/or track a user playing a round of golf, and/or to provide personalized recommendations or analyses to a user. For example, the golf clubs 102 can be associated with a user and each of the golf clubs can have a sensor module 110 affixed thereto and the electronic device(s) 120 can be a mobile phone, wristband, watch, or any other suitable portable communication device that can be carried or worn by the user that is capable of wireless transmission/reception. The electronic device(s) 120 can be configured to determine its location (e.g., using GPS). For example, each sensor module 110 can be secured or affixed to or embedded in a proximal end of a golf club where the handle or grip is disposed, in the shaft of the golf club, and/or in the head of the golf club. The user can interact with the user's electronic device 120 to set up the system 100 for use with the golf clubs 102. For example, the electronic device 120 can be programmed and/or configured to prompt the user to enter information about the golf clubs when it receives transmissions from the sensor modules 110. Upon completion of the set up process, the electronic device 120 associates each of the sensor modules 110 with the corresponding golf clubs 102 to which the sensor modules 110 are affixed based on the unique identifiers, such that when the electronic device 120 receives a subsequent transmission from one of the sensor modules 110, the electronic device 120 can be programmed to identify the golf club used by the user to generate the information included in the subsequent transmission.

As the user plays a round of golf, the system 100 can provide personalized recommendations, e.g., from the environment 10 to the electronic device(s) 120, and can monitor and/or track which golf clubs were used by the golfer for which holes and shots, a distance the golf ball traveled for each shot, locations of the user, holes that have been completed by the user, holes that the user still has to complete, a golf score of the user, and/or other performance information associated with the round of golf being played by the user.

The electronic device(s) 120 can store the performance information associated with the golf round and/or can render one or more GUIs that can be viewed by the user during and/or after the golf round along with personalized recommendations or analyses. In some embodiments, the electronic device(s) 120 can transmit the performance information to the environment 10 for further processing and/or storage. The user may access the environment 10 through the electronic device(s) 120 to review, modify, update, delete, share, and the like, the performance information captured by the system 100, and/or to receive personalized recommendations or analyses before, during, or after a round of golf.

The environmental sensors 130 can be disposed in one or more geographic locations. For example, the environment sensors 130 can be disposed at golf courses and/or weather stations to sense and/or measure environmental conditions that can be used to form the environmental data. The environmental sensors can include, for example, moisture sensors, temperature sensors, wind sensors, solar/light sensors, barometers, and the like. The environmental sensors 130 can be configured to output the environmental conditions, directly or indirectly, to the environment.

Figure 3:
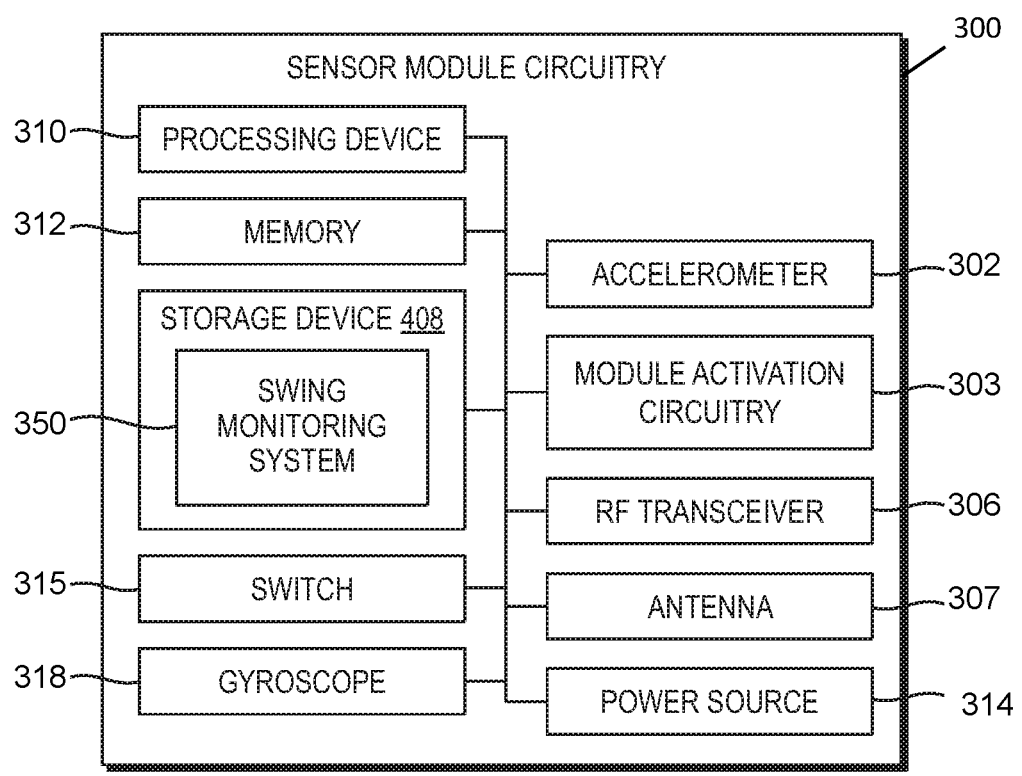
FIG. 3 is a block diagram of sensor module circuitry that can be disposed within a sensor module in accordance with embodiments of the present disclosure.

FIG. 3 is a block diagram of sensor module circuitry 300 that can be disposed within a sensor module attached to or embedded in a golf club (e.g., the grip, shaft, or head) in accordance with embodiments of the present disclosure. The sensor module circuitry 300 can include a multi-axis accelerometer 302, module activation circuitry 303, a radio frequency (RF) transceiver 306 or acoustic transducers, a storage device 308, a processing device 310, memory 312 (e.g., RAM), a power source 314, and a switch 315. In some embodiments, the sensor module circuitry 300 can include a gyroscope 318 in addition to, or in the alternative to, the multi-axis accelerometer 302.

The multi-axis accelerometer 302 can include three or more axes of measurement and can output one or more signals corresponding to each axes of measurement and/or can output one or more signals corresponding to an aggregate or combination of the three axes of measurement. For example, in some embodiments, the accelerometer 302 can be a three-axis or three-dimensional accelerometer that includes three outputs (e.g., the accelerometer can output X, Y, and Z data). The accelerometer 302 can detect and monitor a magnitude and direction of acceleration, e.g., as a vector quantity, and/or can sense an orientation, vibration, and/or shock. For example, in exemplary embodiments, the accelerometer 302 can be used by the sensor module circuitry 300 determine an orientation and/or acceleration of an golf club to which the sensor module including the sensor module circuitry 300 is affixed. In some embodiments, the gyroscope 318 can be used instead or in addition to the accelerometer 302, to determine an orientation of an golf club to which the sensor module including the sensor module circuitry 300 is affixed. The orientation of the golf club can be used to determine when the user is preparing to swing the golf club and/or to identify and discriminate between different phases of a swing (e.g., back swing, forward swing). The acceleration can be used to determine when an impact occurs during a swing, a speed of the swing, a tempo of the swing, and/or any other motion parameters associated with swinging the golf club.

The acceleration and/or velocity can be used to identify and discriminate between different phases of a swing and determine whether an impact between the golf club and an object constitutes a shot. For example, during the backswing phase, a positive linear acceleration can be detected by the accelerometer. Approximately midway through the backswing, the velocity curve changes direction when the club slows down as it reaches the top of the backswing. When the curve changes direction, the acceleration is zero and linear velocity begins to decrease resulting in deceleration. At the end of the backswing phase, the club is temporarily static as the golf club changes direction, and therefore, no velocity is detected based on an output of the accelerometer 302. The downswing begins from the top of the backswing and as the club begins to move in a positive direction towards the ball, the linear acceleration increases. As the velocity approaches a constant value the rate of acceleration slowly begins to decrease and the downswing phase ends when an initial discontinuity in motion is detected by the accelerometer. This discontinuity marks the impact phase of the golf swing and the beginning of the follow through phase of the golf swing.

The module activation circuitry 303 can receive one or more output signals (e.g., X, Y, Z data) from the accelerometer 302 (or gryroscope 318) as inputs to the module activation circuitry 303 and can process the signals to determine whether the golf club to which the sensor module is affixed is within a specified addressing range for a specified period of time. In exemplary embodiments, the module activity circuitry can output one or more signals to the processing device 310 in response to the processing of the signals from the accelerometer 303 (or gyroscope 318). The processing device 310 can use the signals from the module activation circuitry to change a mode of operation of the sensor module circuitry (e.g., from a sleep mode of operation to a normal mode of operation or vice versa). While exemplary embodiments have been illustrated to include module activation circuitry, those skilled in the art will recognize that, in exemplary embodiments, the processing device 310 may be programmed and/or configured to process the output signals of the accelerometer 302 (or gyroscope 318) to determine when to change the mode of operation of the sensor module circuitry.

The RF transceiver 306 can be configured to transmit (e.g., via a transmitter of the RF transceiver) and/or receive (e.g., via a receiver of the RF transceiver) wireless transmissions via an antenna 307. For example, the RF transceiver 306 can be configured to transmit one or more messages, directly or indirectly, to one or more electronic devices (e.g., electronic devices 120) and/or to receive one or more messages, directly or indirectly, from one or more electronic devices. The RF transceiver 306 can be configured to transmit and/or receive messages having at a specified frequency and/or according to a specified sequence and/or packet arrangement. As one example, the RF transceiver 306 can be a BlueTooth® transceiver configured to conform to a BlueTooth® wireless standard for transmitting and/or receiving short-wavelength radio transmissions typically in the frequency range of approximately 2.4 gigahertz (GHz) to approximately 2.48 GHz. As another example, the RF transceiver 306 can be a Wi-Fi transceiver (e.g., as defined IEEE 802.11 standards), which may operate in an identical or similar frequency range as BlueTooth®, but with higher power transmissions. Some other types of RF transceivers 306 that can be implemented by the sensor module circuitry includes RF transceivers configured to transmit and/or receive transmissions according to the Zigbee® communication protocol, and/or any other suitable communication protocol.

The storage device 308 can include any suitable, non-transitory computer-readable storage medium, e.g., read-only memory (ROM), erasable programmable ROM (EPROM), electrically-erasable programmable ROM (EEPROM), flash memory, and the like. In exemplary embodiments, a swing monitoring system 350 can be embodied as computer-readable/executable program code stored on the non-transitory computer-readable storage device 308 and implemented using any suitable, high or low level computing language and/or platform, such as, e.g., Java, C, C++, C#, assembly code, machine readable language, and the like.

The memory 312 can include any suitable non-transitory computer-readable storage medium (e.g., random access memory (RAM), such as, e.g., static RAM (SRAM), dynamic RAM (DRAM), and the like). In some embodiments, the data/information and/or executable code for implementing the system 350 can be retrieved from the storage device 308 and copied to memory 312 during and/or upon implementation of the processes described herein. Once the data/information has be used, updated, modified, replaced, and the like, the data/information may be copied from memory 312 to the storage device 308.

The processing device 310 can include any suitable single- or multiple-core microprocessor of any suitable architecture that is capable of implementing and/or executing the system 350. The processing device 310 can be programmed and/or configured to execute the system 350 to implement one or more processes for monitoring and/or tracking usage of golf clubs by a user and communicating (e.g., via the RF transceiver 306) information corresponding to the usage of the golf clubs with other devices (e.g., the electronic device 120). The processing device 310 can retrieve information/data from, and store information/data to, the storage device 308 and/or memory 312. For example, user performance information, golf course information, performance statistics, user profiles, performance analysis, and/or any other suitable information/data for implemented the system 350 or that may be used by the system 350 may be stored on the storage device 308 and/or a memory 312. Some examples of performance information and/or performance analysis can include, for example, data output by the accelerometer 302 (or gyroscope 318), an indication of a detected impact (e.g., a determined based on the data output by the accelerometer 302 or gyroscope 318), a golf shot (e.g., a determined based on the data output by the accelerometer 302 or gyroscope 318), a golf score, a swing tempo, swing velocity, swing force, club face angle, swing plane, and/or impact force with which the golf club strikes or will strike an object, and/or any other swing parameters as well as club consistency (e.g., variations in shot distances), putting stats (e.g., average putts per hole, 2- putt percentage, 3+ putt-percentage, 1 putt per round, etc.), scrambling statistics (e.g., the golfer's ability to get par when hitting the green in regulation is missed), sand saves (e.g., the ability of a golfer to get par when the ball lands in a bunker during a hole), fairway hits (e.g., percentage of times a golfer hits the fairway when the golf ball is hit from the tee), and the like.

In exemplary embodiments, the processing device 310 can be programmed to execute the system 350 to receive and process information/data from the accelerometer 302 (e.g. X, Y, Z data), RF transceiver 306, storage device 308, and/or memory 312 and/or can be programmed to output information/data to the RF transceiver 306, the storage device 308, and/or the memory 312 based on the execution of the system 350. As one example, the processing device 310 can receive information/data from the accelerometer 302 corresponding to a direction force along one or more of the axes of the accelerometer 302, and can transmit the information data to the electronic device via the RF transceiver 306. As another example, the processing device 310 can receive information/data from the accelerometer 302 corresponding to a direction force along one or more of the axes of the accelerometer 302, can process the information/data to generate an indicator associated with an impact between the golf club to which the sensor module is secured and an object, and can transmit the indicator to the electronic device via the RF transceiver 306.

The power source 314 can be implemented as a battery or capacitive elements configured to store an electric charge. As one example, in some embodiments, the power source can be a button cell lithium battery, such as a CR2032 battery or a CR2354 battery. In some embodiments, the battery may be replaceable by the user. As another example, in some embodiments, the power source 314 can be a rechargeable power source, such as a battery or one or more capacitive elements configured to be recharged via a connection to an external power supply and/or to be recharged by an energy harvesting device. As one example, the rechargeable power source can be recharged using solar energy (e.g., by incorporating photovoltaic or solar cells on the housing on the sensor module), through physical movement (e.g., by incorporating a piezo-electric elements in the sensor module), and/or through any other suitable energy harvesting techniques using any suitable energy harvesting devices.

The switch 315 can be operatively coupled to the processing device 310 to trigger one or more operations by the processing device 310. In some embodiments, the switch 315 can be implemented as a momentary push button, rocker, and/or toggle switch that can be activated by a user. For example, in exemplary embodiments, the switch 315 can be activated by the user to instruct the processing device 310 to transmit an association or initial setup message via the RF transceiver 306. The association or initial setup message can be used to pair the sensor module with an electronic device. In some embodiments, the association or initial setup message can be transmitted according to a BlueTooth® pairing scheme or protocol.

Figure 4A:
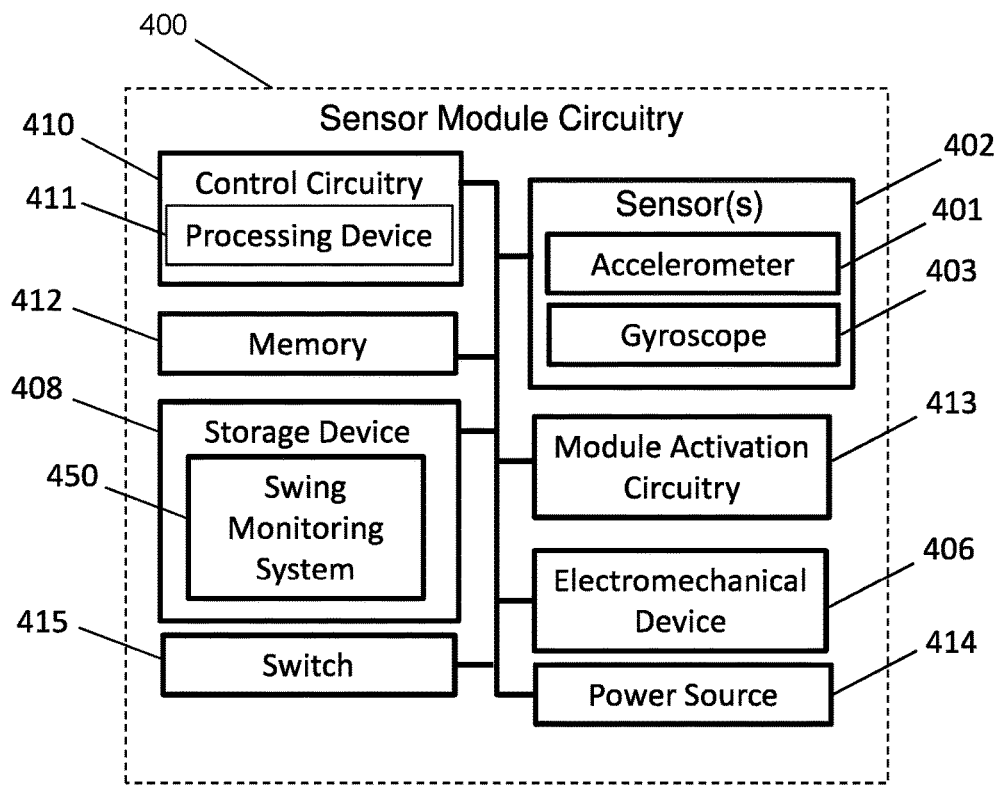
FIG. 4A is a block diagram of another configuration of sensor module circuitry that can be disposed within a sensor module in accordance with embodiments of the present disclosure.

FIG. 4A is a block diagram of another exemplary embodiment of the sensor module circuitry 400 that can be disposed within or on the grip, shaft, or head of a golf club. The sensor module circuitry 400 can include one or more sensors 402 (e.g., accelerometer 401, gyroscope 403, and/or any other suitable sensor), a electromechanical device 406, a storage device 408, control circuitry 410, memory 412 (e.g., RAM), a power source 414, and a switch 415.

The one or more sensors 402 can sense/detect one or more parameters associated with a use of the golf clubs, such as an acceleration, velocity, angular acceleration, orientation, position, impacts between the golf clubs and objects, and the like. The one or more sensors 402 can generate an output, e.g., including one or more sensor signals (e.g., electrical signals or otherwise), to the control circuitry 410. While the one or more sensors 402 are illustrated as including the accelerometer 401 and/or the gyroscope 403, the one or more sensors 402 can include more or fewer sensors. For example, in exemplary embodiments, the one or more sensors 402 can include any one of the accelerometer 401, gyroscope 403, and/or any suitable sensor, such as a magnetometer, pressure sensor, and/or capacitive sensor; any combination of sensors 402, such as any combination of the accelerometer 401, gyroscope 403, magnetometer, capacitive sensor, pressure sensor, etc.)

The multi-axis accelerometer 401 can include three or more axes of measurement and can output one or more signals corresponding to each axes of measurement and/or can output one or more signals corresponding to an aggregate or combination of the three axes of measurement. For example, in some embodiments, the accelerometer 401 can be a three-axis or three-dimensional accelerometer that includes three outputs (e.g., the accelerometer can output X, Y, and Z data). The accelerometer 401 can detect and monitor a magnitude and direction of acceleration, e.g., as a vector quantity, and/or can sense an orientation, vibration, and/or shock. For example, in exemplary embodiments, the accelerometer 401 can be used by the sensor module circuitry 400 determine an orientation and/or acceleration of an golf club to which the sensor module including the sensor module circuitry 400 is affixed or within which the sensor module is embedded (e.g., in the grip shaft, or head). In some embodiments, the gyroscope 403 can be used instead or in addition sensor module is embedded the accelerometer 401, to determine an orientation of an golf club to which the sensor module including the sensor module circuitry 400 is affixed and/or embedded. The orientation of the golf club can be used to determine when the user is preparing to swing the golf club and/or to identify and discriminate between different phases of a swing (e.g., back swing, forward swing). The acceleration can be used to determine when an impact occurs during a swing, a speed of the swing, a tempo of the swing, and/or any other motion parameters associated with swinging the golf club.

The acceleration and/or velocity can be used to identify and discriminate between different phases of a swing and determine whether an impact between the golf club and an object constitutes a shot. For example, during the backswing phase, a positive linear acceleration can be detected by the accelerometer. Approximately midway through the backswing, the velocity curve changes direction when the club slows down as it reaches the top of the backswing. When the curve changes direction, the acceleration is zero and linear velocity begins to decrease resulting in deceleration. At the end of the backswing phase, the club is temporarily static as the golf club changes direction, and therefore, no velocity is detected based on an output of the accelerometer 401. The downswing begins from the top of the backswing and as the club begins to move in a positive direction towards the ball, the linear acceleration increases. As the velocity approaches a constant value the rate of acceleration slowly begins to decrease and the downswing phase ends when an initial discontinuity in motion is detected by the accelerometer. This discontinuity marks the impact phase of the golf swing and the beginning of the follow through phase of the golf swing.

The electromechanical device 406 can be configured to generate pressure waves that propagate through air. The pressure waves can be formed by movement (e.g. vibrations) of the electromagnetic device 406 in response to electrical control signals (e.g., received from the control circuitry 410). For example, the electromechanical device can include a flexible diaphragm that vibrates in response to control signals to generate the pressure waves. The pressure waves generated by the movement of the electromechanical device 406 can form alternating compressions and rarefactions in the air with a frequency (e.g., measured in hertz), amplitude/pressure (e.g., measured in decibels), and phase (e.g., measured in radian or degrees). In exemplary embodiments, the electromechanical device 406 can be a loud/audio speaker or a piezoelectric device. The pressure waves generated by the electromagnetic device 406 can be sound waves. The pressure waves generated by the electromechanical device 406 can be detected by one or more electronic devices (e.g., electronic devices 120) to convey information to the electronic devices.

In some embodiments, the electromechanical device 406 can be configured and/or controlled to generate pressure waves that have a frequency that is above that which can be heard or perceived by some, most, or all humans (i.e. inaudible). As one example, in some embodiments, the electromechanical device 406 can generate pressure waves having a frequency of greater than approximately fifteen kilohertz or greater than approximately twenty kilohertz. As another example, in some embodiments, the electromechanical device can generate pressure waves having a frequency of approximately twenty kilohertz to approximately twenty-five kilohertz. As another example, the electromechanical device 406 can generate pressure waves having a frequency of approximately ten kilohertz to approximately sixty kilohertz. By generating pressure waves at a frequency that is above that which cannot be heard or perceived by some, most, or all humans (i.e. inaudible), exemplary embodiments of the present disclosure advantageously allow the sensor modules (i.e. via the electromechanical device) to communicate with a remote electronic device (i.e. via an electroacoustic transducer of the electronic device) without distracting a user before, during, and/or after swinging or otherwise using the golf clubs to which the sensor modules are affixed or embedded and/or or affecting a performance of the user before, during, and/or after swinging or otherwise using the golf clubs to which the sensor modules are affixed or embedded.

In some embodiments, the electromechanical device 406 can be configured and/or controlled to generate pressure waves that have a frequency that is within a frequency range that can be heard or perceived by some, most, or all humans (i.e. audible). For example, in some embodiments, the frequency of the pressure waves can be less than, e.g., approximately ten kilohertz, approximately fifteen kilohertz, or less than approximately twenty kilohertz. In some embodiments, to reduce and/or minimize distractions to a user, a pressure wave generated at a frequency that is audible to a user can be generated for a short duration of time (e.g., seconds or less), can be generated after the golf swing is completed, and/or can be generated to have an amplitude that results in a low decibel level to minimize and/or reduce distractions to a user.

In some embodiments, the electromechanical device 406 can be configured and/or controlled to generate pressure waves having audible or inaudible frequency that convey information that can be extracted by an electronic device that is separate, distinct, and spaced away from the sensor module. In some embodiments, the parameters of the pressure wave (e.g., amplitude, phase, frequency) can include the information that can be extracted by the electronic device. In some embodiments, the pressure wave can be modulated (e.g., using amplitude modulation, phase modulation, and/or frequency modulation) to encode information, which can be extracted by the electronic device. In some embodiments, the timing of the generation of the pressure waves can be controlled such that the pressure waves are generated after an impact between the golf club and an object is detected, after a golf swing is completed, and/or at any other suitable time. In some embodiments, the duration of the pressure wave (whether it has a frequency that is audible or inaudible) can be controlled. For example, in some embodiments, a pressure wave having a duration that is less than one second can be generated (e.g., a fraction of a second) and the pressure wave can include information that can be extracted by the electronic device, such as which sensor module generated the pressure wave, whether an impact between the golf club and an object was detected by the sensor module, swing analysis information, and/or any other suitable information. By generating a pressure wave that has a duration of a fraction of a second, the sensor module can reduce/minimize power consumption, and for embodiments that generate pressure waves having a frequency that is audible can minimize or reduce the likelihood that the pressure wave will distract a user.

The storage device 408 can include any suitable, non-transitory computer-readable storage medium, e.g., read-only memory (ROM), erasable programmable ROM (EPROM), electrically-erasable programmable ROM (EEPROM), flash memory, and the like. In exemplary embodiments, a swing monitoring system 450 can be embodied as computer-readable/executable program code stored on the non-transitory computer-readable storage device 408 and implemented using any suitable, high or low level computing language and/or platform, such as, e.g., Java, C, C++, C#, assembly code, machine readable language, and the like.

The memory 412 can include any suitable non-transitory computer-readable storage medium (e.g., random access memory (RAM), such as, e.g., static RAM (SRAM), dynamic RAM (DRAM), and the like). In some embodiments, the data/information and/or executable code for implementing the system 450 can be retrieved from the storage device 408 and copied to memory 412 during and/or upon implementation of the processes described herein. Once the data/information has be used, updated, modified, replaced, and the like, the data/information may be copied from memory 412 to the storage device 408.

The control circuitry 410 can include one or more logic-based devices, such as logic gates, flip-flops, field programmable logic arrays, timing generators, processing devices (e.g., microprocessors, digital signal processors, graphical processing units, microcontrollers), and/or any other suitable logic-based devices. In some embodiments, the processing device 411, memory 412, and possibly the storage 408, can be integrated in a single package or can be packaged separately and electrically coupled to each other through traces in a printed circuit board. In exemplary embodiments, at least a portion of the control circuitry 410 can be implemented as a processing device 411, which can include any suitable single- or multiple-core microprocessor of any suitable architecture that is capable of implementing and/or executing the system 450. The processing device 411 can be programmed and/or configured to execute the system 450 to implement one or more processes for monitoring and/or tracking usage of golf clubs by a user and to control the electromechanical device 406 to generate pressure waves corresponding to the usage of the golf clubs. The processing device 411 can retrieve information/data from, and store information/data to, the storage device 408 and/or memory 412. For example, user performance information, golf course information, performance statistics, user profiles, performance analysis, and/or any other suitable information/data for implemented the system 450 or that may be used by the system 450 may be stored on the storage device 408 and/or a memory 412. Some examples of performance information and/or performance analysis can include, for example, data output by the one or more sensors 402, an indication of a detected impact (e.g., a determined based on the data output by the one or more sensors 402), a golf shot (e.g., a determined based on the data output by the one or more sensors 402), a golf score, a swing tempo, swing velocity, swing force, club face angle, swing plane, and/or impact force with which the golf club strikes or will strike an object, and/or any other swing parameters as well as club consistency (e.g., variations in shot distances), putting stats (e.g., average putts per hole, 2– putt percentage, 3+ putt-percentage, 1 putt per round, etc.), scrambling statistics (e.g., the golfer's ability to get par when hitting the green in regulation is missed), sand saves (e.g., the ability of a golfer to get par when the ball lands in a bunker during a hole), fairway hits (e.g., percentage of times a golfer hits the fairway when the golf ball is hit from the tee), and the like.

In exemplary embodiments, the processing device 411 can be programmed to execute the system 450 to receive and process information/data from the one or more sensors 402, storage device 408, and/or memory 412; can be programmed to output control signals to the electromechanical device 406 to control the electromechanical device 406 to generate pressure waves to convey information/data to the electronic devices based on the execution of the system 450; and can be programmed to output data/information to the storage device 408 and/or the memory 412 based on the execution of the system 450. As one example, when the one or more sensors 402 includes the accelerometer 401, the processing device 411 can receive information/data output from the accelerometer corresponding to a direction force along one or more of the axes of the accelerometer 401, and can control the electromechanical device 406 to generate pressure waves to convey information/data associated with the output of the accelerometer 401, to an electronic device (e.g., the electronic device(s) 120). As another example, the processing device 411 can receive information/data output from the accelerometer 401 corresponding to a directional force along one or more of the axes of the accelerometer 401; can process the information/data to generate an indicator associated with an impact between the golf club to which the sensor module is secured and an object; and can control the electromechanical device 406 to generate a pressure wave in response to detection of the impact to indicate the impact to the electronic device.

In exemplary embodiments, the control circuitry 410 (e.g., via the processing device 411) can control the electromagnetic device 406 to generate a continuous pressure wave that propagates through air at a frequency, amplitude, and phase. An electronic device can include a transducer for receiving pressure wave and converting the pressure wave to electrical signals. The electronic device can determine from which sensor the pressure wave propagates based on the frequency and can determine based on detection of the pressure wave that an impact between the golf club to which the sensor module is affixed or embedded was detected by the sensor module.

In exemplary embodiments, the control circuitry 410 (e.g., via the processing device 411) can control the electromagnetic device 406 to generate a pressure wave having a modulate frequency, amplitude, or phase to encode information/data generated, derived, or output from the one or more sensors 402 as well as information/data associated with the sensor module. For example, the control circuitry 410 (e.g., via the processing device 411) can control the electromechanical device 406 to generate a pressure wave using frequency modulation, phase modulation, amplitude modulation, and/or a combination of frequency modulation, phase modulation, amplitude modulation. The modulated pressure wave can encode multi-symbol string (e.g., binary or greater) that can be extracted and interpreted by the electronic device. The information/data encoded in the modulated pressure wave can include an identification parameter that identifies which sensor module generated the pressure wave, an indication that the sensor module detected an impact between the golf club to which the sensor module is affixed or embedded, raw sensor data, swing information derived from raw sensor data, and/or any other suitable information/data. An electronic device can detect the modulated pressure wave via a transducer and can determine from which sensor module the pressure wave propagates by demodulating the modulated pressure wave (e.g., after the modulate pressure wave is converted to electrical signals by a transducer of the electronic device) and extracting the identification parameter included in the modulated pressure wave, and/or can extract any other information/data from the demodulated pressure wave. In some embodiments, the electronic device can determine that an impact occurred between the golf club to which the sensor module is affixed or embedded and an object based on detection of the modulated pressure wave from the sensor module (after associating the detected modulate pressure wave with the sensor module based on the identification parameter that is extracted from the modulated pressure wave. In some embodiments, the electronic device can determine that an impact occurred between the golf club to which the sensor module is affixed or embedded and an object by extracting an indication of the impact encoded in the modulated pressure wave. Thus, in some embodiments, information/ data can be determined or derived based on the presence of the pressure wave itself (whether modulated or not); in some embodiments, information/data can be embedded in and extracted from the modulated pressure wave; and/or in some embodiments, some information/data can be embedded in the modulated pressure wave and some information/data can be determined or derived based on the presence of the modulate pressure itself. In some embodiments, the electronic device can determine that an impact occurred between the golf club to which the sensor module is affixed or embedded and an object by extracting an indication of the impact encoded in the modulated pressure wave.

In some embodiments, the control circuitry 410 can include module activation circuitry 413, which can receive one or more output signals (e.g., X, Y, Z data) from the accelerometer 401 (or gyroscope 403) as inputs to the module activation circuitry 413 and can process the signals to determine whether the golf club to which the sensor module is affixed is within a specified addressing range for a specified period of time. In exemplary embodiments, the module activity circuitry 413 can output one or more signals to the processing device 411 in response to the processing of the signals from the accelerometer 401 (or gyroscope 403). The processing device 411 can use the signals from the module activation circuitry to change a mode of operation of the sensor module circuitry (e.g., from a sleep mode of operation to a normal mode of operation or vice versa). While exemplary embodiments have been illustrated to include module activation circuitry, those skilled in the art will recognize that, in exemplary embodiments, the processing device 411 may be programmed and/or configured to process the output signals of the accelerometer 401 (or gyroscope 403) (e.g., without the module activation circuitry 413) to determine when to change the mode of operation of the sensor module circuitry.

Figure 4B:
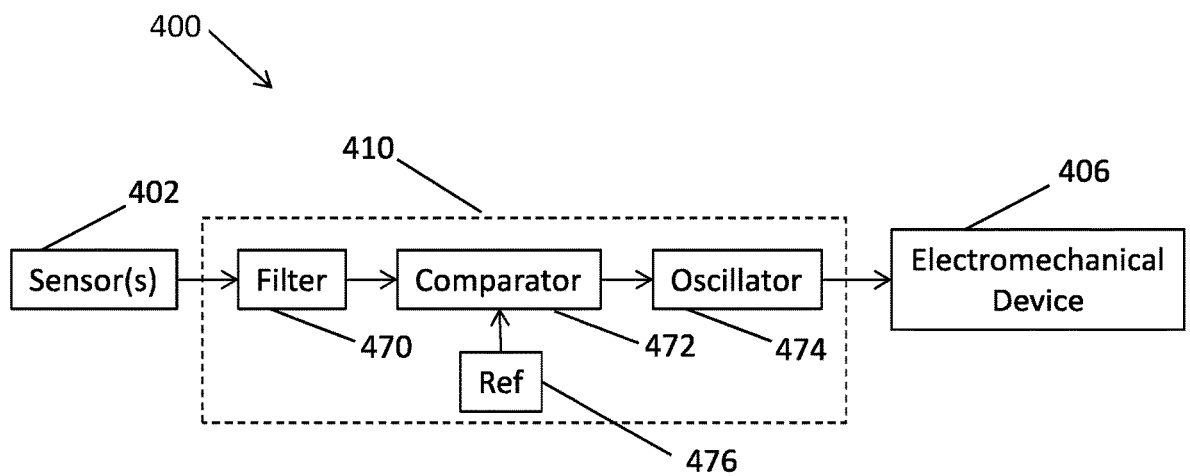
FIG. 4B is a block diagram of another exemplary embodiment of the sensor module circuitry that can be disposed within a sensor module in accordance with embodiments of the present disclosure.

While a non-limiting embodiment of the control circuitry has been illustrated as including a processing device, memory, and storage, exemplary embodiments of the control circuitry can be implemented without a processing device, memory, and/or storage. As one example, the control circuitry can include one or more logic-gates operatively coupled to each other to form a conditional logic circuit that outputs a control signal to the electromechanical device 406 in response to detection of one or more outputs from the one or more sensors 402. For example, during a golf swing the accelerometer can output a first peak acceleration associated with a back swing, which can cause a first condition of the conditional logic circuit to be satisfied; can output a second peak acceleration associated with a forward swing, which can cause a second condition of the conditional logic circuit to be satisfied; and can output a third peak acceleration associated with an impact, which can cause a third condition of the conditional logic circuit to be satisfied. In response to satisfaction of the first, second, and third conditions (e.g., in that sequence), the conditional logic circuit can output a control signal to the electromechanical device 406 to generated a pressure wave (modulated or not). As another example, as shown in FIG. 4B, the control circuitry 410 can include analog circuit elements, e.g., in the form of an amplified analog filter 470 that receives an output from the one or more sensors 402 followed by an analog comparator 472 driving an analog oscillator 474 to control the electromechanical device 406 to generate a pressure wave, e.g., when an impact is occurring or occurred. The comparator 472 can receive as, an input, an output of the filter and a reference generated by reference source 476. The output of the comparator 472 can activate the oscillator or selectively control a connection between the oscillator and the electromechanical device 406 (e.g., a switch) to control pressure wave generation by the electromagnetic device 406.

The power source 414 can be implemented as a battery or capacitive elements configured to store an electric charge. As one example, in some embodiments, the power source can be a button cell lithium battery, such as a CR2032 battery, a CR2354 battery, or any other suitable power source. In some embodiments, the battery may be replaceable by the user. As another example, in some embodiments, the power source 414 can be a rechargeable power source, such as a battery or one or more capacitive elements configured to be recharged via a connection to an external power supply and/or to be recharged by an energy harvesting device. As one example, the rechargeable power source can be recharged using solar energy (e.g., by incorporating photovoltaic or solar cells on the housing on the sensor module), through physical movement (e.g., by incorporating a piezo-electric elements in the sensor module), and/or through any other suitable energy harvesting techniques using any suitable energy harvesting devices.

The switch 415 can be operatively coupled to the processing device 411 to trigger one or more operations by the processing device 410. In some embodiments, the switch 415 can be implemented as a momentary push button, rocker, and/or toggle switch that can be activated by a user. For example, in exemplary embodiments, the switch 415 can be activated by the user to instruct the processing device 411 to control the electromechanical device to generate a pressure wave during an association or initial recognition process to associate the sensor module with an electronic device.

Figure 5:
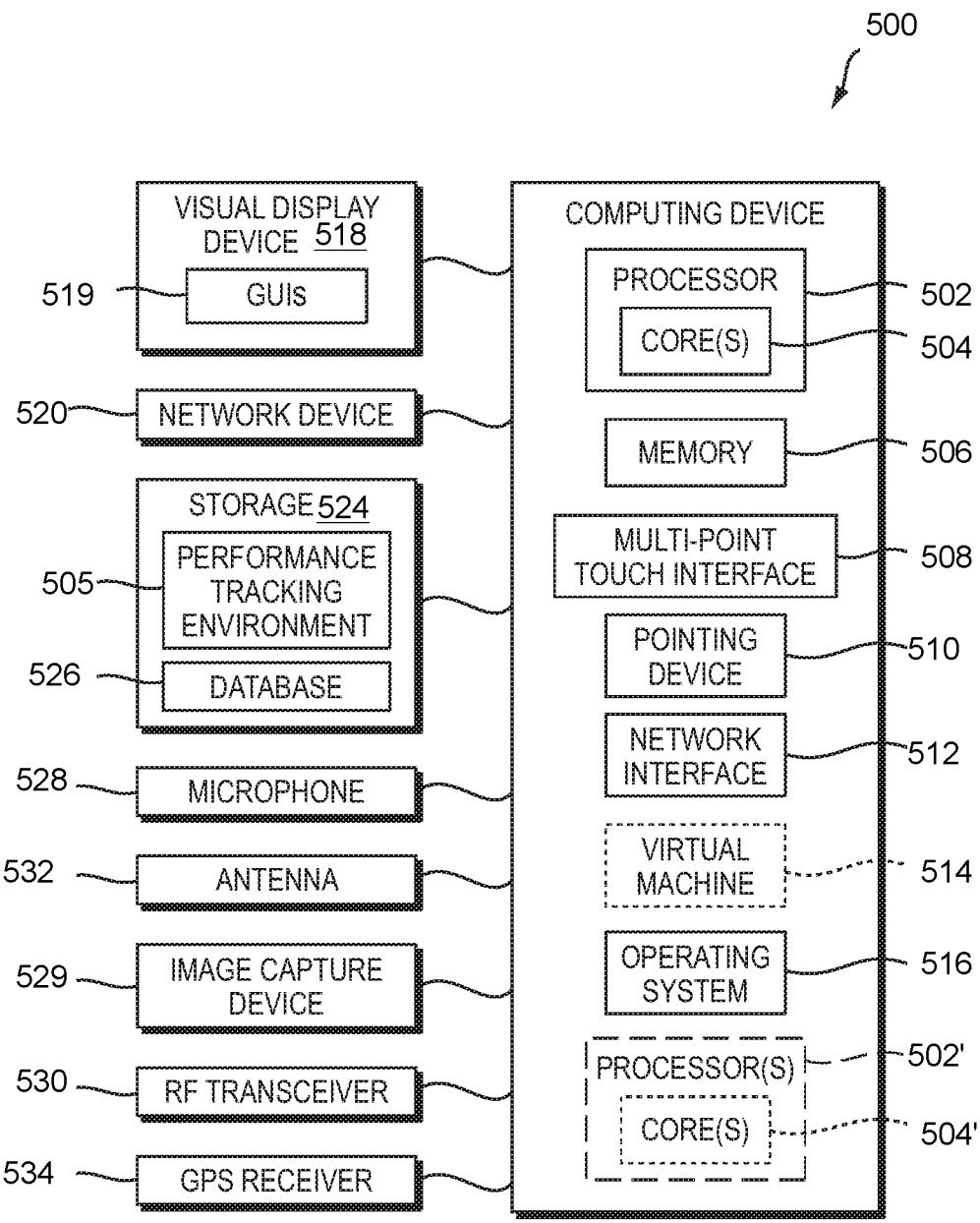
FIG. 5 is a block diagram of an electronic device that can be implemented in the performance monitoring system in accordance with exemplary embodiments of the present disclosure.

FIG. 5 is a block diagram of an exemplary electronic device 500 that may be used to implement an embodiment of the electronic device 120 described herein. The electronic device 500 can include a computing device that includes one or more non-transitory computer-readable media for storing computer-executable instructions, code, or software for implementing a performance tracking and/or monitoring environment 505. The non-transitory computer-readable media may include, but are not limited to, one or more types of hardware memory, non-transitory tangible media (for example, one or more magnetic storage disks, one or more optical disks, one or more flash drives), and the like. For example, memory 506 included in the electronic device 500 may store computer-readable and computer-executable instructions or software for implementing exemplary embodiments of the environment 505. The computing device 500 also includes configurable and/or programmable processing device, e.g., a processor 502 and associated core 504, and optionally, one or more additional configurable and/or programmable processor(s) 502' and associated core(s) 504' (for example, in the case of computer systems having multiple processors/cores), for executing computer-readable and computer-executable instructions or software stored in the memory 506 and other programs for controlling system hardware. Processor 502 and processor(s) 502' may each be a single core processor or multiple core (504 and 504') processor.

Virtualization may be employed in the electronic device 500 so that infrastructure and resources in the electronic device 500 may be shared dynamically. A virtual machine 514 may be provided to handle a process running on multiple processors so that the process appears to be using only one computing resource rather than multiple computing resources. Multiple virtual machines may also be used with one processor.

Memory 506 may include a computer system memory or random access memory, such as DRAM, SRAM, EDO RAM, and the like. Memory 506 may include other types of memory as well, or combinations thereof.

A user may interact with the electronic device 500 through a visual display device 518, such as a touch screen, which may display one or more graphical user interfaces 519 render upon execution of the computer readable instructions, code, or software corresponding to the environment 505. The electronic device 500 may include other I/O devices for receiving input from a user, for example, a keyboard (virtual or physical) or any suitable multi-point touch interface 508, a pointing device 510 (e.g., a mouse or stylus), a microphone 528, and/or an image capturing device 529 (e.g., a camera or scanner). The computing device 500 may include other suitable conventional I/O peripherals.

The electronic device 500 may also include one or more storage devices 524, such as a hard-drive, CD-ROM, or other computer readable media, for storing data and computer-readable instructions and/or software that implement exemplary embodiments of the environment 505 described herein. Exemplary storage device 524 may also store one or more databases for storing any suitable information required to implement exemplary embodiments. For example, exemplary storage device 524 can store one or more databases 526 for storing information, such as user performance information, golf course information, performance statistics, user profiles, performance analysis, and/or any other information to be used by embodiments of the environment 505. The databases may be updated manually or automatically at any suitable time to add, delete, and/or update one or more items in the databases.

The electronic device 500 can include a network interface 512 configured to interface via one or more network devices 520 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 512 may include a built-in network adapter, network interface card, PCMCIA network card, card bus network adapter, wireless network adapter, USB network adapter, modem or any other device suitable for interfacing the computing device 500 to any type of network capable of communication and performing the operations described herein.

In exemplary embodiments, the electronic device 500 can include a RF transceiver 530. The RF transceiver 530 can be configured to transmit and/or receive wireless transmissions via an antenna 532. For example, the RF transceiver can be configured to transmit one or more messages, directly or indirectly, to one or more sensor modules (e.g., sensor modules 110 shown in FIG. 2) and/or to a remote system (e.g., environment 10 shown in FIG. 1) and/or can be configured to receive one or more messages, directly or indirectly, from one or more sensor modules and/or the remote system. The RF transceiver 530 can be configured to transmit and/or receive messages having a specified frequency and/or according to a specified sequence and/or packet arrangement. As one example, the RF transceiver 530 can be a BlueTooth® transceiver configured to conform to a BlueTooth® wireless standard for transmitting and/or receiving short-wavelength radio transmissions typically in the frequency range of approximately 2.4 gigahertz (GHz) to approximately 2.48 GHz. As another example, the RF transceiver 530 can be a Wi-Fi transceiver (e.g., as defined IEEE 802.11 standards), which may operate in an identical or similar frequency range as BlueTooth®, but with higher power transmissions. Some other types of RF transceivers that can be implemented by the sensor module circuitry includes RF transceivers configured to transmit and/or receive transmissions according to the Zigbee communication protocol, and/or any other suitable communication protocol.

The electronic device can include a GPS receiver 534. The GPS receiver 534 can be configured to receive GPS satellite transmissions including GPS data, which can be used by the environment 505 being executed by the processor 502 of the electronic device 500 to monitor and/or track a geographic location of the electronic device 500 (e.g., a longitude and latitude of the electronic device). For example, for embodiments implemented in a golfing environment, the electronic device 500 can receive a broadcast signal from a GPS satellite and can process the GPS data included in broadcast signal to determine a geographic location of the electronic device 500, which can be utilized by the environment 505 to determine a geographic location of the electronic device 500 on a golf course, relative to a hole on the golf course, a distance the electronic device 500 traveled between consecutive golf shots, and/or any other location based information.

The electronic device 500 may be any computer system, such as a laptop, handheld computer, tablet computer (e.g., the iPad™ tablet computer), mobile computing or communication device (e.g., the iPhone™ communication device or an Android™ communication device), or other form of computing or telecommunications device that is capable of communication and that has sufficient processor power and memory capacity to perform the operations described herein. The electronic device 500 may run any operating system 516, such as any of the versions of the Microsoft® Windows® operating systems, the different releases of the Unix and Linux operating systems, any version of the MacOS® for Macintosh computers, any version of the Android operating system, any version of the iOS operating system for the Apple iPhone and/or iPAd, any embedded operating system, any real-time operating system, any open source operating system, any proprietary operating system, or any other operating system capable of running on the computing device and performing the operations described herein. In exemplary embodiments, the operating system 516 may be run in native mode or emulated mode. In an exemplary embodiment, the operating system 516 may be run on one or more cloud machine instances.

In some embodiments, the electronic device 500 can receive RF transmissions from a sensor module and/or can generate data including acceleration information, other swing information, an indication that the sensor module detected an impact between the golf club and an object, and/or an indication of a golf shot. In response to the receipt or generation of the information/data, the processing device 502 of the electronic device 500 can execute the environment 505 to determine whether the impact associated with the received or generated information/data is a false positive golf shot. If the electronic device 500 determines that the impact is a false positive golf shot, the environment 505 can be executed by the processing device 502 to suppress or ignore the data/information included in the transmission or generated by the electronic device 500.

In exemplary embodiments, the processor 502 can "listen" for detection of pressure waves from sensor modules based on an output of the microphone 528. For example, when the environment 505 is being executed in the foreground or background, the processor 802 can monitor an input corresponding to an output of the microphone 528 to determine whether the microphone 528 detected a pressure wave propagating from one or more of the sensor modules (e.g., based on movement or vibrations of the transducer in response to the pressure wave). In response to receipt of electrical signals corresponding to the pressure wave at the input of the processor 502 from the transducer 528, the processor 502 can process the electrical signals to determine information/data based on the receipt of the pressure wave itself and/or based on information/data encode in and extracted from the pressure wave. For example, in some embodiments, the electronic device 500 can detect pressure waves propagating from a sensor module that include acceleration information, other swing information, sensor module identification information, an indication that the sensor module detected an impact between the instrument and an object, and/or an indication of a golf shot.

Figure 6:
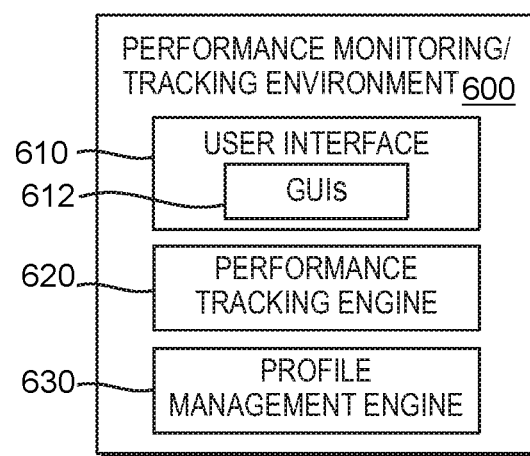
FIG. 6 is a block diagram of an exemplary embodiment of the performance monitoring and/or tracking environment that can be implemented in accordance with the present disclosure.

FIG. 6 is a block diagram of an exemplary embodiment of the performance monitoring and/or tracking environment 505 that can be implemented by embodiments of the electronic device 500 to monitor and/or track a user's golfing performance. The environment 505 can include a user interface 610, a profile management engine 620, and a performance tracking engine 630.

In exemplary embodiments, the user interface 610 can be programmed and/or include executable code to provide one or more graphical user interfaces (GUIs) 612 through which a user can interact with the environment 505. The GUIs 612 displayed to users can include data entry areas to receive information from the user and/or can include data outputs to display information to the user. Some examples of data entry fields include, but are not limited to text boxes, check boxes, buttons, dropdown menus, and/or any other suitable data entry fields.

The profile management engine 620 can be programmed and/or configured to receive, maintain, modify, and/or update a user profile. In exemplary embodiments, the user profile can be created by the user upon an initial execution of the environment 505. As one example, the processing device can execute the engine 620 to request user information including, for example, a user name, gender, weight, height, golf handicap, stance (e.g., right or left), an experience level (e.g., number of years playing, a number of rounds played in the previous year), and/or any other suitable user information. As another example, the processing device can execute the engine 620 to collect and/or setup golf club information including, for example, an identity of the golf clubs to which the sensor modules are or will be affixed, an association between the sensor modules and their corresponding golf clubs, an estimated distance an object (e.g., a golf ball) will likely travel when the user strikes it with each golf club, and/or any other suitable golf club information that can be utilized by the environment 505 to facilitate tracking and/or monitoring a user's performance during an activity (e.g., a round of golf). In exemplary embodiments, the user profile can be maintained, modified, and/or updated to include statistic information related to the user's past performance. In exemplary embodiments, the statistic information can include an average score, a handicap, an average distance an object travels for each of the golf clubs, a user performance on specific golf courses, and/or any other statistic information that can be utilized, maintained, and/or created based on the tracking and/or monitoring of a user's performance during an activity (e.g., a round of golf).

In exemplary embodiments, the performance tracking engine 630 can be programmed and/or configured to receive and/or maintain information corresponding to specific golf courses and/or holes at a specific golf course. For example, the engine 630 can receive and/or maintain a geographic map of the golf course including information related to the terrain of the golf course, a location of the holes on the golf course, a par for the holes on the golf course, and/or any other suitable information related to golf courses. In some embodiments, the golf course information can be maintained in a database of the remote system and the electronic device can request the golf course information from the database in response to an input from the user. In some embodiments, the golf course information can be stored on the electronic device executing the environment 505.

The performance tracking engine 630 can be executed by the processing device to monitor transmissions from sensor modules affixed to the golf clubs and to process the transmissions. For example, in exemplary embodiments, transmissions from the sensor modules can include information corresponding to accelerometer information of the golf club, an indication of an impact between a golf club and an object (e.g., a golf ball or the earth), an indication of a golf shot, swing analysis information (e.g., a swing speed, a swing tempo, swing force, club face angle, swing plane, etc., represented via accelerometer output information), and/or any other suitable information related to an operation of the sensor module and/or a utilization of the golf club. The information received by the electronic device can be utilized upon execution of the engine 630 to identify a location at which a golf shot occurred, identify a number of golf shots that occurred for a particular hole, identify a golf score for a particular hole or course, provide a swing analysis, identify false positive impacts/golf shots (e.g., using criteria described herein), and the like. The information received from the transmissions can also be provided to the engine 630 to create, update, and/or modify statistic information in the user profile.

Figure 7:
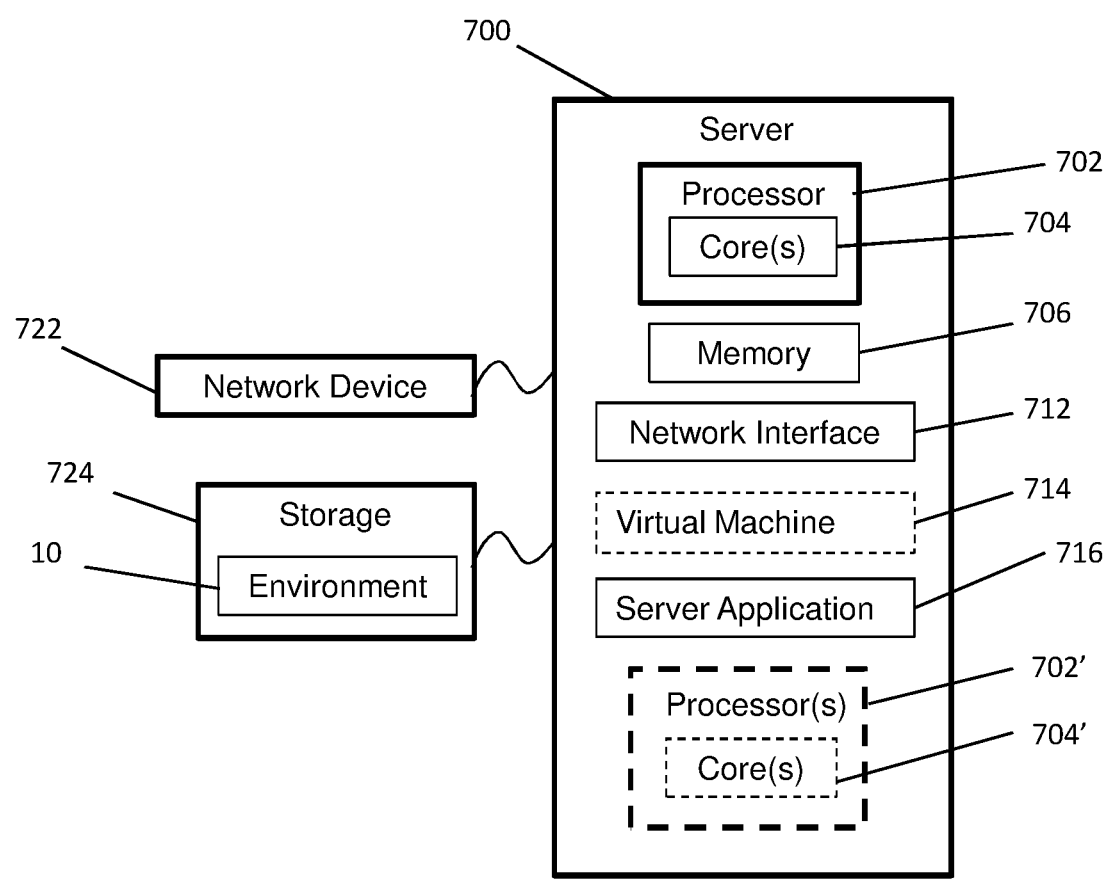
FIG. 7 is a block diagram of an exemplary server in accordance with embodiments of the present disclosure.

FIG. 7 is a block diagram of one of many exemplary servers 700 for implementing embodiments of the environment 10 in accordance with embodiments of the present disclosure. The server 700 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 706 included in the server 700 may store computer-readable and computer-executable instructions or software for implementing exemplary embodiments of the environment 10 or portions thereof.

The server 700 also includes configurable and/or programmable processor 702 and associated core 704, and optionally, one or more additional configurable and/or programmable processor(s) 702' and associated core(s) 704' (for example, in the case of computer systems having multiple processors/cores), for executing computer-readable and computer-executable instructions or software stored in the memory 706 and other programs for controlling system hardware. Processor 702 and processor(s) 702' may each be a single core processor or multiple core (704 and 704') processor.

Virtualization may be employed in the server 700 so that infrastructure and resources in the computing device may be shared dynamically. One or more virtual machines 714 may be provided to handle a process running on multiple processors so that the process appears to be using only one computing resource rather than multiple computing resources, and/or to allocate computing resources to perform functions and operations associated with the environment. Multiple virtual machines may also be used with one processor or can be distributed across several processors.

Memory 706 may include a computer system memory or random access memory, such as DRAM, SRAM, EDO RAM, and the like. Memory 706 may include other types of memory as well, or combinations thereof.

The server 700 may also include one or more storage devices 724, such as a hard-drive, CD-ROM, mass storage flash drive, or other computer readable media, for storing data and computer-readable instructions and/or software that can be executed by the processing device 702 to implement exemplary embodiments of the environment 10 described herein.

The server 700 can include a network interface 712 configured to interface via one or more network devices 722 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections (including via cellular base stations), controller area network (CAN), or some combination of any or all of the above. The network interface 712 may include a built-in network adapter, network interface card, PCMCIA network card, card bus network adapter, wireless network adapter, USB network adapter, modem or any other device suitable for interfacing the server 700 to any type of network capable of communication and performing the operations described herein. While the server 700 depicted in FIG. 7 is implemented as a server, exemplary embodiments of the server 700 can be any computer system, such as a workstation, desktop computer or other form of computing or telecommunications device that is capable of communication with other devices either by wireless communication or wired communication and that has sufficient processor power and memory capacity to perform the operations described herein.

The server 700 may run any server application 716, such as any of the versions of server applications including any Unix-based server applications, Linux-based server application, any proprietary server applications, or any other server applications capable of running on the server 700 and performing the operations described herein. An example of a server application that can run on the computing device includes the Apache server application.

Figure 8:
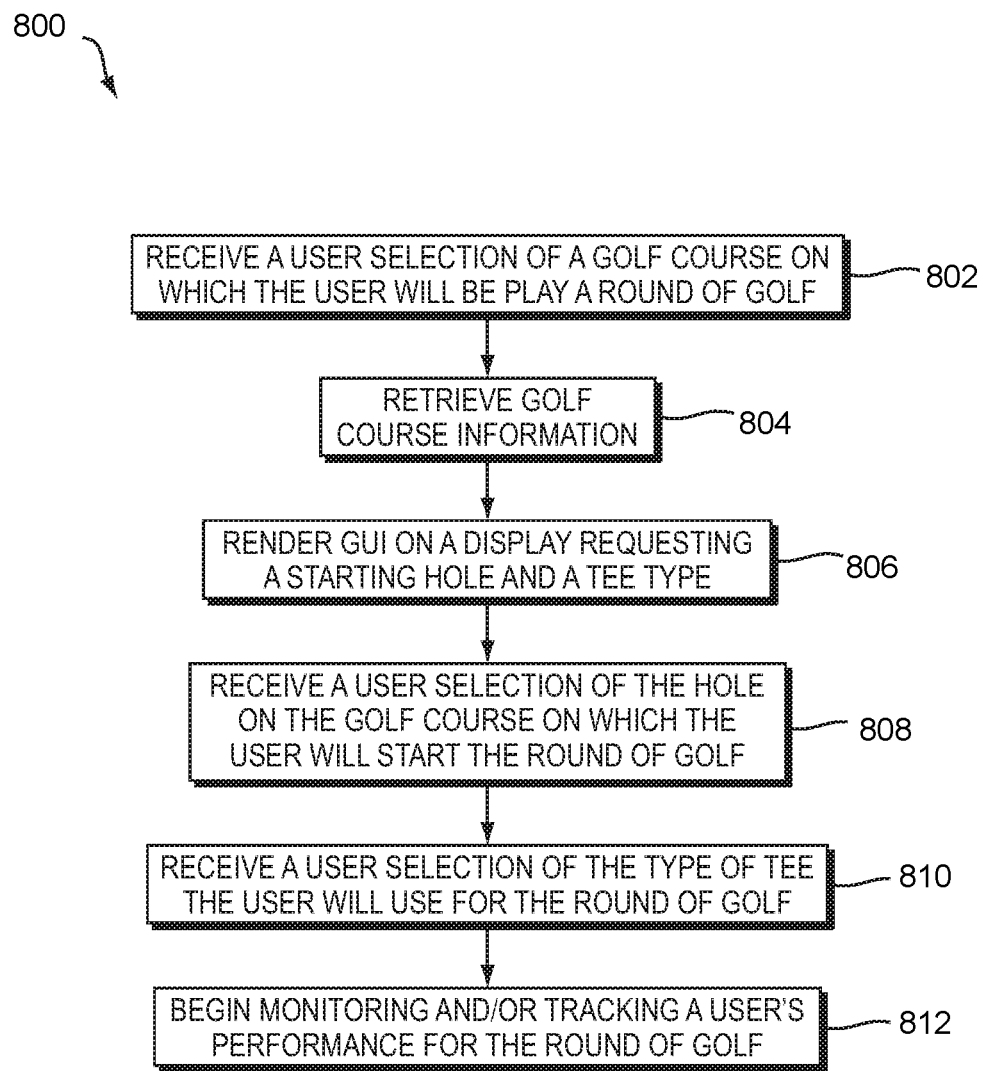
FIG. 8 is a flowchart illustrating a process for utilizing exemplary embodiments of the monitoring and/or tracking environment to initiate the tracking and/or monitoring of a round golf.

FIG. 8 is a flowchart illustrating a process 800 for utilizing exemplary embodiments of the monitoring and/or tracking environment 505 to initiate the tracking and/or monitoring of a round golf. At step 802, the environment 505 being executed by the user's electronic device can receive a user selection of a golf course on which the user will play a round of golf. In response to the user selection, the electronic device can retrieve golf course information from storage at step 804. As one example, the electronic device can execute the environment 505 to retrieve the golf course information corresponding to the selected golf course from a storage device included in the electronic device. As another example, the electronic device can execute the environment 505 to request the golf course information from a remote storage device. In exemplary embodiments, the remote storage device can be part of a remote system (e.g., the environment 10). The electronic device can retrieve the golf course information by transmitting the request to the remote system and the remote system can query a database for the golf course information to retrieve the golf course information from a database. After the remote system retrieves the golf course information, the remote system can transmit a response to the electronic device including the golf course information.

Using the golf course information, the environment 505 can be executed by the electronic device to render a GUI on a display of the electronic device at step 806 requesting the user to select a starting hole for the golf course and a type of tee to be used. At step 808, the environment 505 can receive the user's selection of the hole on the golf course at which the user will start the round of golf and at step 810, the environment 505 can receive the user's selection of the type of tee the user will use for the round of golf. At step 812, the environment can be executed to begin monitoring and/or tracking the user's performance for the round of golf.

Figure 9:
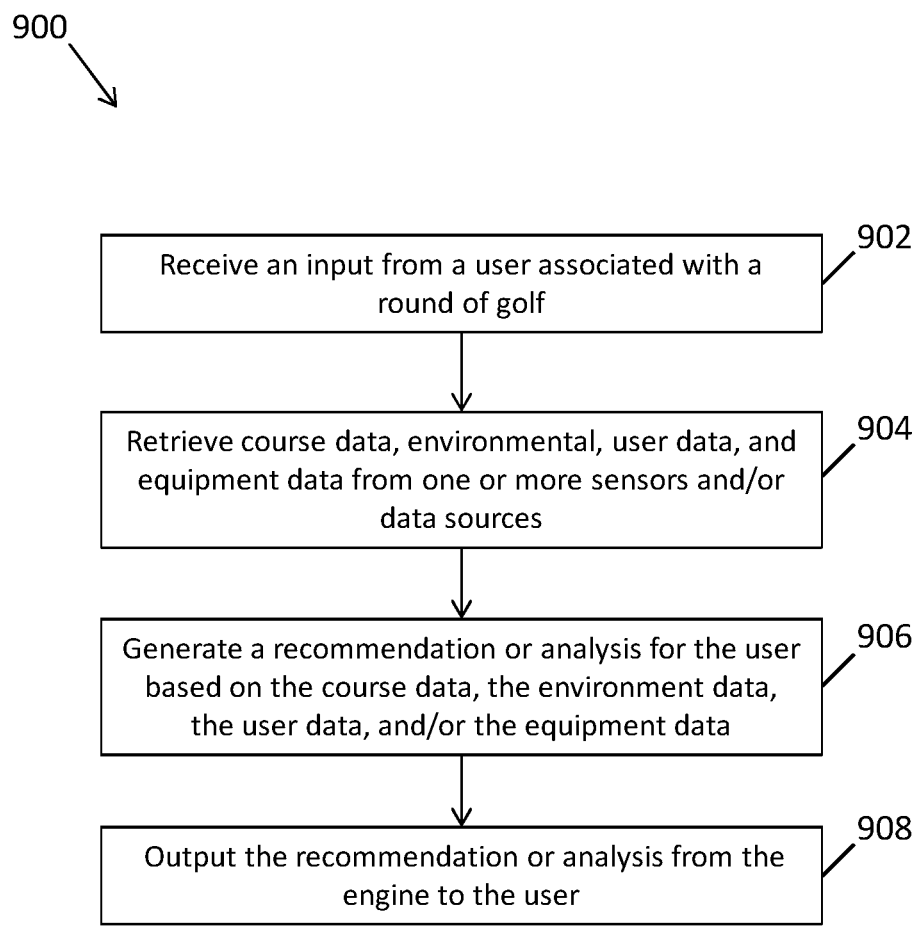
FIG. 9 is a flowchart illustrating a process for providing an autonomous personalized recommendation or analysis to a user before, during, or after a round of golf in accordance with embodiments of the present disclosure.

FIG. 9 is a flowchart illustrating a process 900 for providing an autonomous personalized recommendation or analysis to a user before, during, or after a round of golf in accordance with embodiments of the present disclosure. At step 902, the autonomous golf recommendation and analysis environment can receive an input from a user associated with a round of golf. At step 904, the environment can retrieve course data, environmental, user data, and/or equipment data from one or more sensors and/or one or more data sources. The course data can include data associated with a golf course for the round of golf. The environmental data can include environmental conditions associated with the golf course or a geographic region in proximity to or within which the golf course resides. The user data can include data that is specific to the user's golf performance at the golf course or at other golf courses as well as the performance of other users/golfers at the golf course or at other golf courses. The equipment data can include data that is specific the user's use of his/her golf equipment as well as data associated with the user's golf equipment and the use of identical or similar golf equipment by other users/golfers. At step 906, the environment can execute a recommendation and analysis engine to generate a recommendation or analysis for the user based on the course data, the environment data, the user data, and/or the equipment data. The recommendation or analysis can be autonomously generated by the engine, which can execute one or more machine learning algorithms that consume the course data, the environmental data, the user data, and/or the equipment data. At step 908, the recommendation or analysis can be output from the engine to the user. For example, the recommendation or analysis can be rendered on a display and/or output by a speaker associated with the user's device (e.g., one of the electronic devices).

Figure 10:
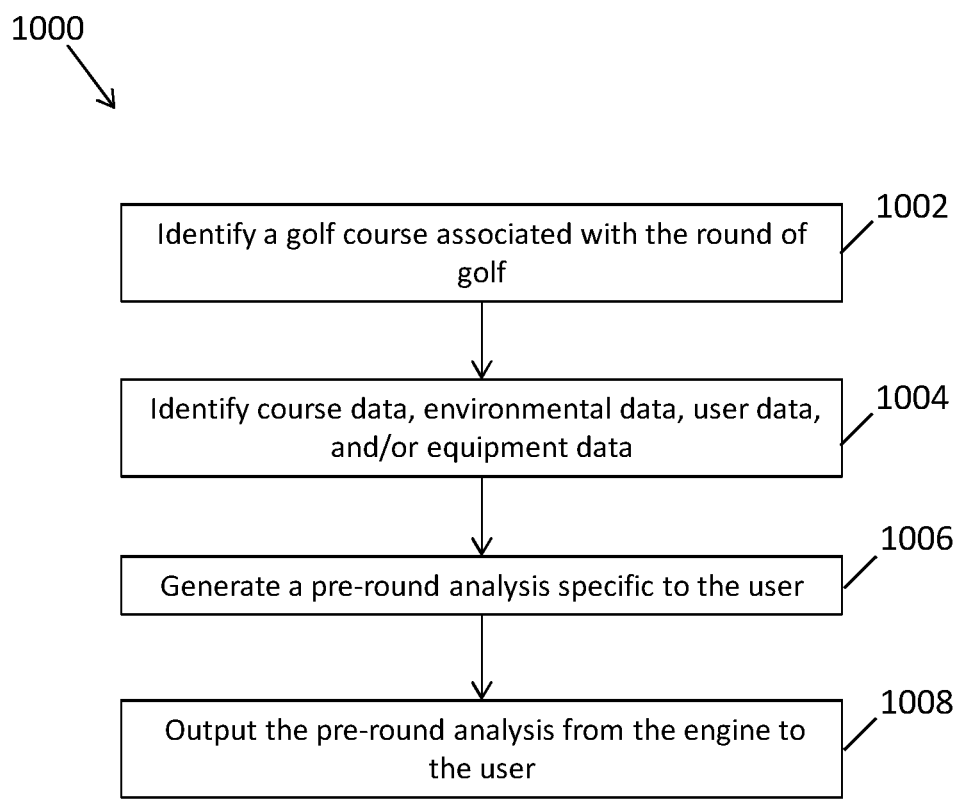
FIG. 10 is a flowchart illustrating a process 1000 for autonomous generation of a recommendation or analysis before a round of golf in accordance with embodiments of the present disclosure.

FIG. 10 is a flowchart illustrating a process 1000 for autonomous generation of a recommendation or analysis before a round of golf in accordance with embodiments of the present disclosure. At step 1002, the autonomous golf recommendation and analysis environment can identify a golf course associated with the round of golf in response to input received from the user. As one example, the environment can receive location information generated by a user's electronic device and the environment can determine whether the location information corresponds to an arrival of the user at a golf course (e.g., based on the location of the electronic device changing to a location that coincides with a golf course location known by the environment). As another example, the user can specify a particular golf course for which a pre-round course analysis is requested. At step 1004, the environment can identify course data, environmental data, user data, and/or equipment data that is specific to the identified golf course and/or that is specific to the user. At step 1006, the environment execute a recommendation and analysis engine to autonomously generate a pre-round analysis specific to the user based on the course data, the environment data, the user data, and/or the equipment data. The recommendation or analysis can be autonomously generated by the engine, which can execute one or more machine learning algorithms that consume the course data, the environmental data, the user data, and/or the equipment data. For example, the multiple machine learning algorithms can be used concurrently or in sequence to generate outputs, and the environment can select which of the outputs to provide to the user based on one or more criteria (e.g., dynamic or static weighting and/or voting models). At step 1008, the pre-round analysis can be output from the engine to the user. For example, the pre-round analysis can be rendered on a display and/or output by a speaker of the user's device (e.g., one of the electronic devices). The pre-round analysis can include strategies for playing a round of golf at the identified golf course including, for example, a preliminary strategy for playing each hole of the golf course (e.g., what clubs to use when, where to hit the golf ball, etc.).

Figure 11:
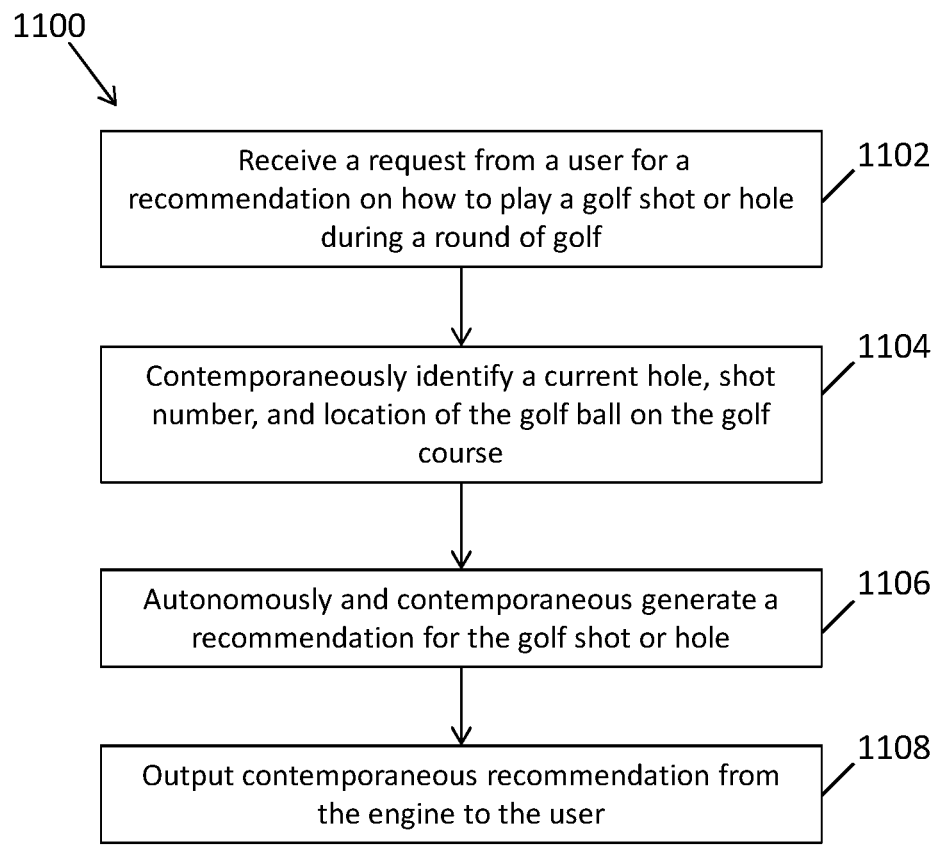
FIG. 11 is a flowchart illustrating a process for autonomous generation of a recommendation or analysis during a round of golf in accordance with embodiments of the present disclosure.

FIG. 11 is a flowchart illustrating a process 1100 for autonomous generation of a recommendation or analysis during a round of golf in accordance with embodiments of the present disclosure. At step 1102, the autonomous golf recommendation and analysis environment can receive a request from a user for a recommendation on how to play a golf shot or hole during a round of golf In response to the request, the environment can contemporaneously identify a current hole, shot number, and location of the golf ball on the golf course at step 1104. For example, the environment can be monitoring and/or tracking the user's round of golf based on data generated by the user's electronic device(s) and/or sensor modules affixed to the golf clubs. At step 1106, the environment can autonomously and contemporaneous generate a recommendation for the golf shot or hole based on the data generated by the electronic device(s) and/or sensor modules up to the time of the request as well as historical and contemporaneous course data, environmental data, user data, and/or equipment data associate the user, other user playing at the golf course contemporaneously with the user, and/or historical data associated with the user's performance at the golf course in the past and/or historical data associated with other users performance at the golf course in the past. The contemporaneous recommendation can be autonomously generated by the engine, which can execute one or more machine learning algorithms that consume the contemporaneous and historical course data, the environmental data, the user data, and/or the equipment data. For example, the multiple machine learning algorithms can be used concurrently or in sequence to generate outputs, and the environment can select which of the outputs to provide to the user based on one or more criteria (e.g., dynamic or static weighting and/or voting models). At step 1108, the contemporaneous recommendation can be output from the engine to the user. For example, the contemporaneous recommendation can be rendered on a display and/or output by a speaker of the user's device (e.g., one of the electronic devices). The contemporaneous recommendation can include strategies for the current golf shot or hole. For example, the contemporaneous recommendation can identify which club to use for the golf shot, a sequence of golf clubs to use on the hole, an estimated distance that the user should hit the golf shot, a direction in which to hit the golf shot, and so on.

Figure 12:
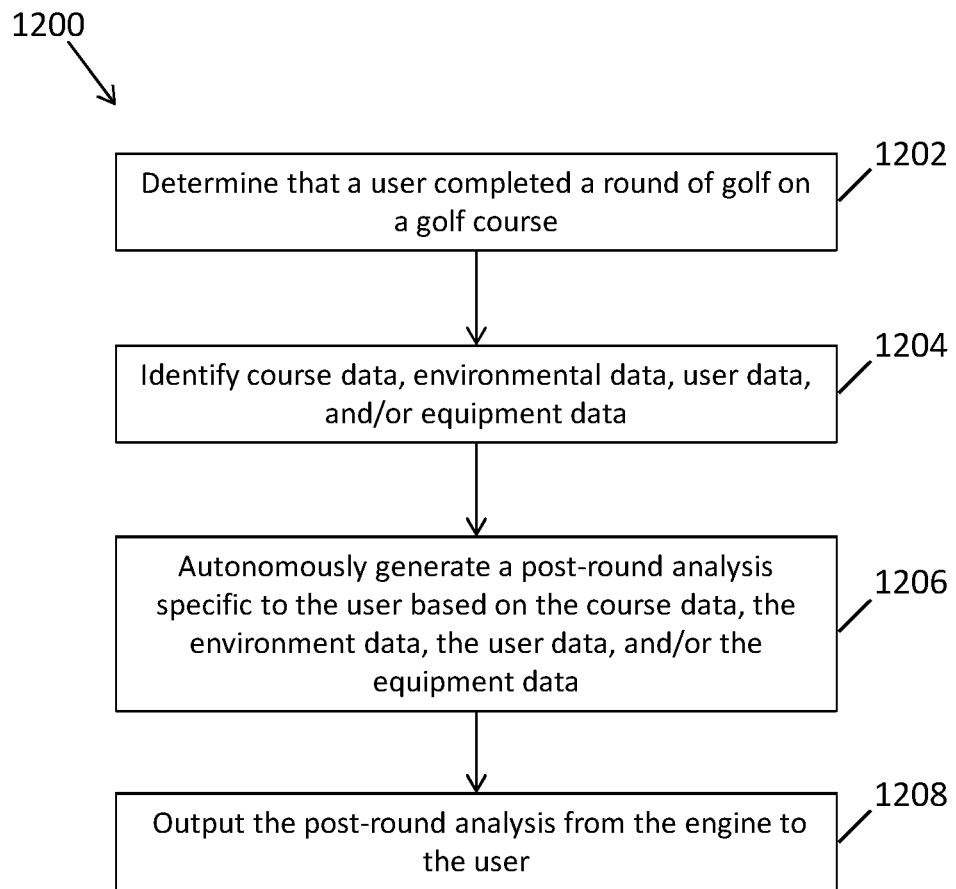
FIG. 12 is a flowchart illustrating a process for autonomous generation of a recommendation or analysis after a round of golf in accordance with embodiments of the present disclosure.

FIG. 12 is a flowchart illustrating a process 1200 for autonomous generation of a recommendation or analysis after a round of golf in accordance with embodiments of the present disclosure. At step 1202, the autonomous golf recommendation and analysis environment can determine that a user completed a round of golf on a golf course in response to input received from the user. As one example, the environment can receive location information and golf data generated by a user's electronic device and/or sensors affixed to the golf clubs, and the environment can determine that the golf data and location information corresponds to a completion of a round of golf at the golf course by the user. As another example, the user can specify that the user completed a round of golf at the golf course as an input. At step 1204, the environment can identify course data, environmental data, user data (include user data generated during the completed round of golf), and/or equipment data (including equipment data generated during the completed round of golf) that is specific to the round of golf at the golf course and/or that is specific to the user. At step 1206, the environment execute a recommendation and analysis engine to autonomously generate a post-round analysis specific to the user based on the course data, the environment data, the user data, and/or the equipment data. The recommendation or analysis can be autonomously generated by the engine, which can execute one or more machine learning algorithms that consume the course data, the environmental data, the user data, and/or the equipment data. For example, the multiple machine learning algorithms can be used concurrently or in sequence to generate outputs, and the environment can select which of the outputs to provide to the user based on one or more criteria (e.g., dynamic or static weighting and/or voting models). At step 1208, the post-round analysis can be output from the engine and rendered on a display of the user. The post-round analysis can include strategies for improving the user performance during the next round of golf at the golf course and/or for improving the user's next round of golf at any golf course. For example, the post-round analysis can identify particular golf shots during the round that may have been improved if a different club was used, or if a different strategy was followed.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other embodiments, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A method of autonomously generating personalized recommendations for a user before, during, or after a round of golf, the method comprising:
    receiving an input from a user associated with a round of golf;
    retrieving at least one of course data, environmental data, user data, or equipment data from at least one of one or more sensors or one or more data sources;
    autonomously generating a recommendation or analysis for the user based on the course data, the environment data, the user data, or the equipment data in response to executing of one or more machine learning algorithms that consume the course data, the environmental data, the user data, and the equipment data; and
    outputting the recommendation or analysis to the user.

2. The method of claim 1, wherein the course data includes data associated with a golf course for the round of golf.

3. The method of claim 1, wherein the environmental data includes environmental conditions associated with the golf course or a geographic region in proximity to or within which the golf course resides.

4. The method of claim 1, wherein the user data includes data that is specific to the golf performance of the user at the golf course or at other golf courses.

5. The method of claim 1, wherein the equipment data includes data that is specific the use of golf equipment by the user.

6. The method of claim 1, wherein the one or more machine learning algorithms are executed concurrently to each other.

7. The method of claim 6, further comprising:
    weighting the outputs of the one or more machine learning algorithms.

8. The method of claim 6, further comprising:
    assigning each output of the one or more machine learning algorithms a vote; and
    determine the recommendation or analysis to output to be rendered on the display based on a quantity of votes.

9. The method of claim 1, wherein a pre-round analysis is autonomously generated, and the method further comprises:
    identifying a golf course associated with the round of golf in response to input received from the user.

10. The method of claim 9, wherein identifying the golf course comprises:
    receiving location information generated by an electronic device associated with the user; and
    determining whether the location information corresponds to an arrival of the user at a golf course.

11. The method of claim 1, wherein a post-round analysis is autonomously generated, and the method further comprises:
    receiving location information and golf data generated by at least one of an electronic device associated with the user or sensors affixed to golf clubs associated with the user; and
    determining that the golf data and location information corresponds to a completion of a round of golf at the golf course by the user.

12. The method of claim 1, wherein a contemporaneous recommendation is autonomously generated during the round of golf, and the method comprises:
    identifying a current hole, shot number, and location of the golf ball on the golf course.

13. The method of claim 12, further comprising:
    tracking the round of golf based on data generated by at least one of an electronic device associated with the user or sensors affixed to golf clubs associated with the user.

14. A system for autonomously generating personalized recommendations for a user before, during, or after a round of golf, the system comprising:
    one or more non-transitory computer-readable media storing at least one of course data, environmental data, user data, or equipment data;
    one or more servers configured to:
    receive an input from a user associated with a round of golf;
    retrieve the course data, the environmental data, the user data, or the equipment data from the one or more non-transitory computer-readable media;
    autonomously generate a recommendation or analysis for the user based on the course data, the environment data, the user data, or the equipment data in response to executing of one or more machine learning algorithms that consume the course data, the environmental data, the user data, and the equipment data; and
    output the recommendation or analysis to the user.

15. The system of claim 14, wherein the course data includes data associated with a golf course for the round of golf, the environmental data includes environmental conditions associated with the golf course or a geographic region in proximity to or within which the golf course resides, the user data includes data that is specific to the golf performance of the user at the golf course or at other golf courses, and the equipment data includes data that is specific the use of golf equipment by the user.

16. The system of claim 14, wherein the one or more servers are configured to execute the one or more machine learning algorithms concurrently with each other.

17. The system of claim 16, wherein the one or more servers are configured to weight the outputs of the one or more machine learning algorithms.

18. The system of claim 16, wherein the one or more servers are configured to assign each output of the one or more machine learning algorithms a vote and determine the recommendation or analysis to output to be rendered on the display based on a quantity of votes.

19. The system of claim 14, wherein a pre-round analysis is autonomously generated, and the one or more servers are configured to:
    identify a golf course associated with the round of golf in response to input received from the user.

20. The system of claim 19, wherein the one or more servers are configured to identify the golf course by receiving location information generated by an electronic device associated with the user, and determining whether the location information corresponds to an arrival of the user at a golf course.

21. The system of claim 14, wherein a post-round analysis is autonomously generated, and the one or more servers are configured to:
    receive location information and golf data generated by at least one of an electronic device associated with the user or sensors affixed to golf clubs associated with the user; and
    determine that the golf data and location information corresponds to a completion of a round of golf at the golf course by the user.

22. The system of claim 14, wherein a contemporaneous recommendation is autonomously generated during the round of golf, and the one or more servers are configured to:
   identify a current hole, shot number, and location of the golf ball on the golf course.

23. The system of claim 22, wherein the one or more servers are configured to:
   track the round of golf based on data generated by at least one of an electronic device associated with the user or sensors affixed to golf clubs associated with the user.

* * * * *